(12) United States Patent
Muto et al.

(10) Patent No.: US 10,007,709 B2
(45) Date of Patent: Jun. 26, 2018

(54) INFORMATION PROCESSING DEVICE AND INFORMATION PROCESSING METHOD

(71) Applicant: Seiko Epson Corporation, Shinjuku-ku (JP)

(72) Inventors: Nobuo Muto, Matsumoto (JP); Megumi Sano, Kawasaki (JP); Yoichi Hirabayashi, Matsumoto (JP); Masahisa Ikejiri, Fuchu (JP)

(73) Assignee: SEIKO EPSON CORPORATION, Tokyo (JP)

( * ) Notice: Subject to any disclaimer, the term of this patent is extended or adjusted under 35 U.S.C. 154(b) by 532 days.

(21) Appl. No.: 14/562,480

(22) Filed: Dec. 5, 2014

(65) Prior Publication Data

US 2015/0161911 A1    Jun. 11, 2015

(30) Foreign Application Priority Data

Dec. 6, 2013  (JP) .................................. 2013-252755

(51) Int. Cl.

| G09B 19/00 | (2006.01) |
| G06F 17/30 | (2006.01) |
| G06F 19/00 | (2018.01) |
| G01G 19/00 | (2006.01) |
| A61B 5/053 | (2006.01) |
| G01G 19/44 | (2006.01) |
| A61B 5/03 | (2006.01) |

(52) U.S. Cl.
CPC .... *G06F 17/30554* (2013.01); *G06F 19/3475* (2013.01); *G06F 19/3481* (2013.01); *A61B 5/03* (2013.01); *A61B 5/0531* (2013.01); *G01G 19/00* (2013.01); *G01G 19/44* (2013.01)

(58) Field of Classification Search
CPC .......................... G09B 19/0092; G06F 19/3475
USPC ........................................................ 434/127
See application file for complete search history.

(56) References Cited

U.S. PATENT DOCUMENTS 4,576,244 A  *  3/1986  Zeigner .................. G01G 19/44
                                                                    177/245
4,629,015 A  *  12/1986  Fried ....................... A61M 1/16
                                                                    128/DIG. 13

(Continued)

FOREIGN PATENT DOCUMENTS

| JP | 2001-286446 A | 10/2001 |
| JP | 2002-095643 A | 4/2002 |
| JP | 2009-521050 A | 5/2009 |

*Primary Examiner* — Robert J Utama
(74) *Attorney, Agent, or Firm* — Kilpatrick Townsend & Stockton LLP

(57) ABSTRACT

An information processing device includes: a user information acquisition unit which acquires first information, second information, and third information about a user; a correlation information acquisition unit which acquires correlation information representing a relation between the first information, the second information, and the third information; an initial value setting unit which sets an initial value of the first information, the second information, and the third information; a fixing designation unit which designate fixing of the first information; a change designation unit which designates change of the second information; and an update unit which updates the third information on the basis of the correlation information.

9 Claims, 18 Drawing Sheets

(56) References Cited

U.S. PATENT DOCUMENTS

| | | | | |
|---|---|---|---|---|
| 4,694,922 | A * | 9/1987 | Mairot | G01G 19/44 |
| | | | | 177/178 |
| 6,369,337 | B1 * | 4/2002 | Machiyama | A61B 5/0537 |
| | | | | 177/245 |
| 2002/0022773 | A1 * | 2/2002 | Drinan | A61B 5/0537 |
| | | | | 600/300 |
| 2004/0035611 | A1 * | 2/2004 | Honda | A61B 5/0537 |
| | | | | 177/25.19 |
| 2004/0238228 | A1 * | 12/2004 | Montague | G01G 19/44 |
| | | | | 177/25.13 |
| 2005/0113650 | A1 * | 5/2005 | Pacione | A61B 5/411 |
| | | | | 600/300 |
| 2008/0004501 | A1 * | 1/2008 | Gavrilov | G01G 19/4146 |
| | | | | 600/300 |
| 2008/0306767 | A1 | 12/2008 | Bodlaender et al. | |
| 2009/0118589 | A1 * | 5/2009 | Ueshima | A61B 5/0002 |
| | | | | 600/300 |
| 2010/0130831 | A1 * | 5/2010 | Sato | G01G 19/4146 |
| | | | | 600/300 |
| 2011/0106553 | A1 * | 5/2011 | Sato | A61B 5/0537 |
| | | | | 705/2 |
| 2011/0143322 | A1 * | 6/2011 | Tsang | G06F 19/3475 |
| | | | | 434/127 |
| 2011/0301916 | A1 * | 12/2011 | Oshima | G01G 19/50 |
| | | | | 702/173 |
| 2012/0004570 | A1 * | 1/2012 | Shimizu | A61B 5/0537 |
| | | | | 600/547 |
| 2013/0131463 | A1 * | 5/2013 | Date | G01G 19/50 |
| | | | | 600/301 |
| 2014/0212850 | A1 * | 7/2014 | Shimizu | G01G 19/50 |
| | | | | 434/127 |

* cited by examiner

|  | TARGET BODY WEIGHT IS FIXED | TARGET PERIOD IS FIXED | ZONE STAYING TIME IS FIXED |
|---|---|---|---|
| USER CHANGES TARGET BODY WEIGHT | — | CALCULATE AND REPORT ZONE STAYING TIME | · CALCULATE AND REPORT TARGET PERIOD<br>OR<br>· REPORT INTERCEPT AND SLOPE OF WEIGHT LOSS LINE<br>OR<br>· REPORT COORDINATES (START POINT, END POINT) |
| USER CHANGES TARGET PERIOD | · CALCULATE AND REPORT ZONE STAYING TIME<br>OR<br>· REPORT INTERCEPT AND SLOPE OF WEIGHT LOSS LINE<br>OR<br>· REPORT COORDINATES (START POINT, END POINT) | — | · CALCULATE AND REPORT TARGET BODY WEIGHT<br>OR<br>· REPORT INTERCEPT AND SLOPE OF WEIGHT LOSS LINE<br>OR<br>· REPORT COORDINATES (START POINT, END POINT) |
| USER CHANGES ZONE STAYING TIME | · CALCULATE AND REPORT TARGET PERIOD<br>OR<br>· REPORT INTERCEPT AND SLOPE OF WEIGHT LOSS LINE<br>OR<br>· REPORT COORDINATES (START POINT, END POINT) | · CALCULATE AND REPORT TARGET BODY WEIGHT<br>OR<br>· REPORT INTERCEPT AND SLOPE OF WEIGHT LOSS LINE<br>OR<br>· REPORT COORDINATES (START POINT, END POINT) | — |

FIG. 11

| | TARGET BODY WEIGHT (kg) | | | | | | | | | | | | | | |
|---|---|---|---|---|---|---|---|---|---|---|---|---|---|---|---|
| | 40 | 41 | 42 | 43 | 44 | 45 | 46 | 47 | 48 | 49 | 50 | 51 | 52 | 53 | 54 |
| | −15kg | −14kg | −13kg | −12kg | −11kg | −10kg | −9kg | −8kg | −7kg | −6kg | −5kg | −4kg | −3kg | −2kg | −1kg |
| 1 MONTH | 30 | 24 | 19.2 | 15.4 | 12.3 | 9.8 | 7.8 | 6.2 | 5 | 4 | 3.2 | 2.6 | 2.1 | 1.7 | 1.4 |
| 2 MONTHS | 28 | 22.4 | 17.9 | 14.3 | 11.4 | 9.1 | 7.3 | 5.8 | 4.6 | 3.7 | 3 | 2.4 | 1.9 | 1.5 | 1.2 |
| 3 MONTHS | 26 | 20.8 | 16.6 | 13.3 | 10.6 | 8.5 | 6.8 | 5.4 | 4.3 | 3.4 | 2.7 | 2.2 | 1.8 | 1.4 | 1.1 |
| 4 MONTHS | 24 | 19.2 | 15.4 | 12.3 | 9.8 | 7.8 | 6.2 | 5 | 4 | 3.2 | 2.6 | 2.1 | 1.7 | 1.4 | 1.1 |
| 5 MONTHS | 22 | 17.6 | 14.1 | 11.3 | 9 | 7.2 | 5.8 | 4.6 | 3.7 | 3 | 2.4 | 1.9 | 1.5 | 1.2 | 1 |
| 6 MONTHS | 20 | 16 | 12.8 | 10.2 | 8.2 | 6.6 | 5.3 | 4.2 | 3.4 | 2.7 | 2.2 | 1.8 | 1.4 | 1.1 | 0.9 |
| 7 MONTHS | 18 | 14.4 | 11.5 | 9.2 | 7.4 | 5.9 | 4.7 | 3.8 | 3 | 2.4 | 1.9 | 1.5 | 1.2 | 1 | 0.8 |
| 8 MONTHS | 16 | 12.8 | 10.2 | 8.2 | 6.6 | 5.3 | 4.2 | 3.4 | 2.7 | 2.2 | 1.8 | 1.4 | 1.1 | 0.9 | 0.7 |
| 9 MONTHS | 14 | 11.2 | 9 | 7.2 | 5.8 | 4.6 | 3.7 | 3 | 2.4 | 1.9 | 1.5 | 1.2 | 1 | 0.8 | 0.6 |
| 10 MONTHS | 12 | 9.6 | 7.7 | 6.2 | 5 | 4 | 3.2 | 2.6 | 2.1 | 1.7 | 1.4 | 1.1 | 0.9 | 0.7 | 0.6 |
| 11 MONTHS | 10 | 8 | 6.4 | 5.1 | 4.1 | 3.3 | 2.6 | 2.1 | 1.7 | 1.4 | 1.1 | 0.9 | 0.7 | 0.6 | 0.5 |
| 12 MONTHS | 8 | 6.4 | 5.1 | 4.1 | 3.3 | 2.6 | 2.1 | 1.7 | 1.4 | 1.1 | 0.9 | 0.7 | 0.6 | 0.5 | 0.4 |
| 13 MONTHS | 6 | 4.8 | 3.8 | 3 | 2.4 | 1.9 | 1.5 | 1.2 | 1 | 0.8 | 0.6 | 0.5 | 0.4 | 0.3 | 0.2 |
| 14 MONTHS | 4 | 3.2 | 2.6 | 2.1 | 1.7 | 1.4 | 1.1 | 0.9 | 0.7 | 0.6 | 0.5 | 0.4 | 0.3 | 0.2 | 0.2 |
| 15 MONTHS | 2 | 1.6 | 1.3 | 1 | 0.8 | 0.6 | 0.5 | 0.4 | 0.3 | 0.2 | 0.2 | 0.2 | 0.2 | 0.2 | 0.2 |

TARGET PERIOD

FIG. 12

INFORMATION PROCESSING DEVICE AND INFORMATION PROCESSING METHOD

The entire disclosure of Japanese Patent Application No. 2013-252755, filed Dec. 6, 2013 is expressly incorporated by reference herein.

BACKGROUND

1. Technical Field

The present invention relates to an information processing device and an information processing method.

2. Related Art

Recently, with the increasing interest in health care, services and systems to assist in maintenance and enhancement of health are becoming used broadly. While various techniques for such services and systems are conceivable, a technique using personal information of a user as a subject is used in consideration of improvement in accuracy or the like of advice information provided by such services.

For example, JP-A-2002-95643 discloses a body fat measuring device and a body fat measuring method in which a target value is calculated variably. According to JP-A-2002-95643, on the basis of a preset target value of body weight, body fat mass or the like (target body weight) and a target exercise period (target period), a zone staying time for the user to achieve the target value is set. The zone staying time is updated every time body information is measured, and what extent of exercise is needed from now on is predicted.

However, in the technique of JP-A-2002-95643, a zone staying time that is predicted to match the present status after an exercise is actually carried out, that is, the time during which a proper exercise is carried out, is calculated. Therefore, it is difficult to know a proper target period or target body weight in advance.

Also, since a target body weight and a target period are fixed and a zone staying time corresponding to body information in each round of measurement is calculated, target setting in which a value involved in the calculation of the target such as a decision on target body weight based on target period and zone staying time is changed flexibly, cannot be realized.

Moreover, it is difficult to review changes in the time during which a proper exercise is carried out (zone staying time) due to daily changes or the like in the user's physical condition and environment, and targets such as target body weight and target period, and to set a target value that matches the body and circumstance each time.

SUMMARY

An advantage of some aspects of the invention is to solve at least a part of the problems described above, and the invention can be implemented as the following forms or application examples.

APPLICATION EXAMPLE 1

This application example is directed to an information processing device including: a user information acquisition unit which acquires first information, second information, and third information about a user; a correlation information acquisition unit which acquires correlation information representing a relation between the first information, the second information, and the third information; an initial value setting unit which sets an initial value of the first information, the second information, and the third information; a fixing designation unit which designates fixing of the first information; a change designation unit which designates change of the second information; and an update unit which updates the third information on the basis of the correlation information.

According to this application example, the user can change, by himself/herself, the first information, the second information and the third information and thus can make a target visible. Since assistance can be provided in reasonable and effective target setting in which an achievable target for the user is set, the user will be motivated further. For example, target setting in which a value involved in target calculation such as a decision on a target value (exercise information) based on target information and body information is changed flexibly, can be realized. Also, body weight and body fat mass can be predicted without re-measurement. Moreover, a predictive simulation can be conducted before an exercise is carried out.

APPLICATION EXAMPLE 2

This application example is directed to the information processing device according to the application example described above, wherein the first information, the second information, and the third information is information about one of body information, exercise information, and target information of the user, and that is different from each other.

According to this application example, target setting in which a value involved in target calculation such as a decision on a target value (exercise information) based on target information and body information is changed flexibly, can be realized.

APPLICATION EXAMPLE 3

This application example is directed to the information processing device according to the application example described above, wherein the user information acquisition unit acquires the first information, the second information, and the third information of the past, present, or future.

According to this application example, the first information, the second information, and the third information of the past, present, or future can be acquired, and therefore a target can be made visible.

APPLICATION EXAMPLE 4

This application example is directed to the information processing device according to the application example described above, wherein the information processing device further includes a display unit, and the display unit displays a designation result by at least one of the fixing designation unit and the change designation unit, and the third information that is updated by the update unit.

According to this application example, a user-friendly user interface that visually presents information to the user can be provided.

APPLICATION EXAMPLE 5

This application example is directed to the information processing device according to the application example described above, wherein the designation result and the third information that is updated are expressed using a chart on the display unit.

According to this application example, a user-friendly user interface that visually presents information to the user with a chart and allows the user to change the chart can be provided.

APPLICATION EXAMPLE 6

This application example is directed to the information processing device according to the application example described above, wherein the information processing device further includes a communication unit, and the correlation information acquisition unit acquires the correlation information from the communication unit.

According to this application example, a user-friendly user interface that acquires the correlation information from the communication unit can be provided.

APPLICATION EXAMPLE 7

This application example is directed to the information processing device according to the application example described above, wherein the initial value setting unit sets an initial value of the first information, the second information, and the third information on the basis of the body information of the user.

According to this application example, assistance can be provided in reasonable and effective target setting in which an achievable target for the user is set.

APPLICATION EXAMPLE 8

This application example is directed to an information processing method including: acquisition processing to acquire staying time information representing a time during which a pulse rate of a user is within a predetermined zone, body information representing a present value of body weight or body fat mass of the user, and target information representing a target value of the body weight or the body fat mass of the user and a target period that is a period until the target value is achieved; processing to create advice information about weight loss, on the basis of a relation expression which expresses a relation between a fluctuation in the body weight or the body fat mass of the user and the staying time information, and the information acquired in the acquisition processing; and output processing to output the advice information that is created. The method causes a computer to execute: processing to create fixing designation information to designate fixing of one of the three kinds of information of the staying time information, the target value, and the target period, and generate modification designation information to designate modification of one of the remaining two; and processing to request again for the other of the remaining two on the basis of the one of the three kinds of information after the fixing and the remaining two of the three kinds of information after the modification, in the case where acquisition processing is carried out to acquire the one of the three kinds of information that is fixed on the basis of the fixing designation information and acquisition processing is carried out to acquire the one of the remaining two that is modified on the basis of the modification designation information.

According to this application example, the user can change, by himself/herself, the first information, the second information, and the third information, and thus can make a target visible. Since assistance can be provided in reasonable and effective target setting in which an achievable target for the user is set, the user will be motivated further. Such an information processing method can be realized by executing a program.

APPLICATION EXAMPLE 9

This application example is directed to the information processing method according to the application example described above, wherein if a value corresponding to a cumulative value of the staying time information during a predetermined period is T_zone, an amount of fluctuation in the body weight or the body fat mass of the user during the predetermined period is W, and a fat burning coefficient is Kfat, the relation expression is T_zone×Kfat=W.

According to this application example, the staying time information and the fluctuation in the body weight or the like can be associated with each other, using the relational expression.

BRIEF DESCRIPTION OF THE DRAWINGS

The invention will be described with reference to the accompanying drawings, wherein like numbers reference like elements.

FIG. 11 shows the relation between target body weight, target period, and zone staying time.

FIG. 12 is a table to find zone staying time on the basis of target body weight and target period.

DESCRIPTION OF EXEMPLARY EMBODIMENTS

Figure 1:
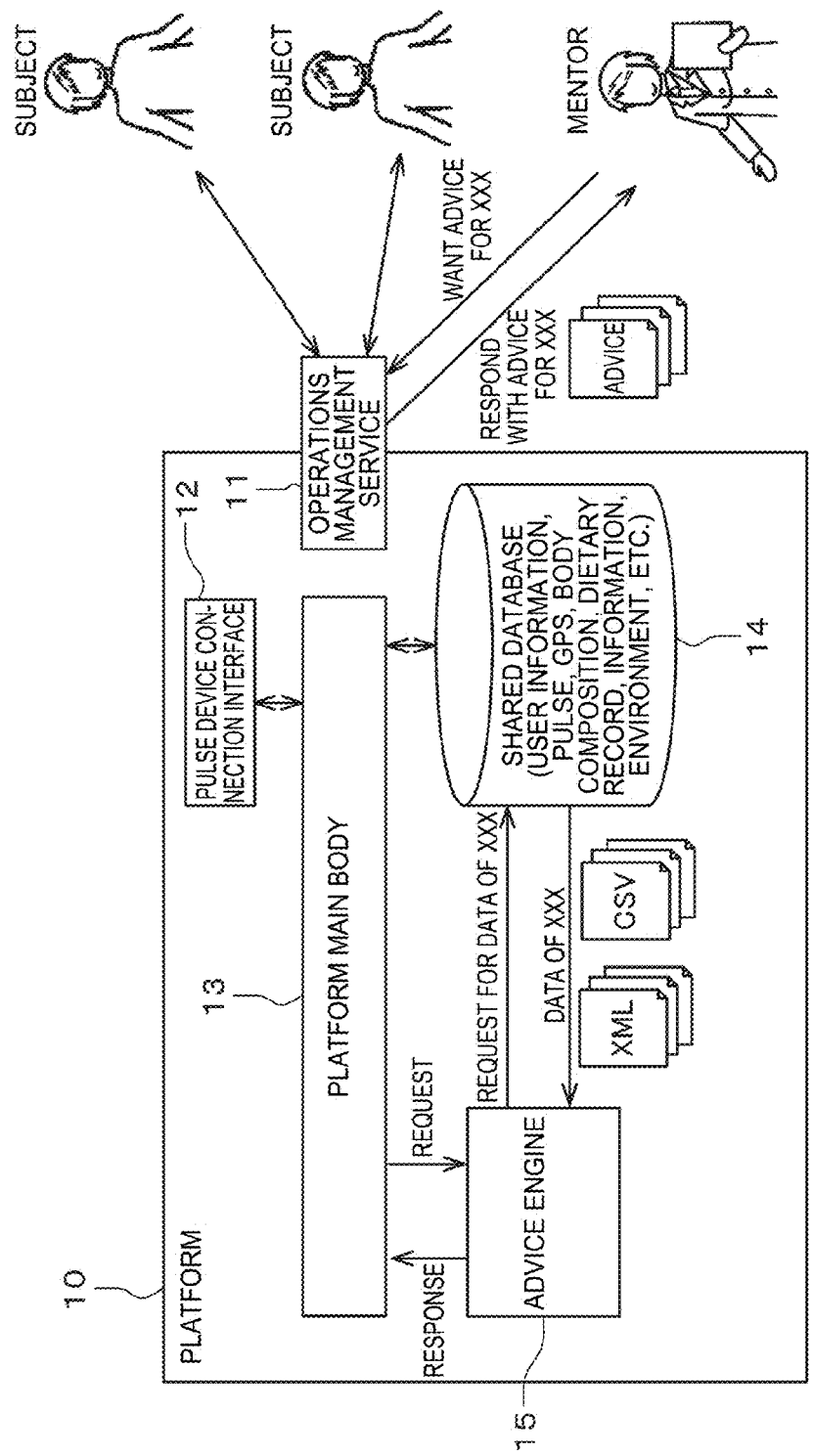
FIG. 1 illustrates an example of data flows in the technique according to an embodiment.

Hereinafter, an embodiment will be described. The embodiment described below should not unduly limit the contents of the invention described in the appended claims. Not all the configurations described in the embodiment are essential components of the invention.

1. Technique of this Embodiment

First, the technique of this embodiment will be described.

Recently, with the increasing public awareness of health, services or the like for maintenance and enhancement of health are becoming provided broadly. For example, as the term of metabolic syndrome has become widely known with respect to obesity, many users periodically measure values of their body weights and abdominal girths. However, even if measured values are obtained, it is difficult for users who are not medical experts to properly reflect fluctuations in the measured values on their lifestyles. Ideally, experts such as doctors should be consulted for advice. However, considering the burden on experts who are in charge of many subjects, and problems such as cost, there is great demand for a system that automates generation of advance information to a certain extent.

Also, various factors such as exercise and diet are considered to be contributing to fluctuations in body weight or the like. Therefore, in generating proper advice information, it is important to acquire the exercise state and dietary circumstance of the user. If a sensor is worn by the user, the exercise state can be analyzed on the basis of sensor information from the sensor. For example, if a pedometer (in a broad sense, an activity meter) is realized as an acceleration sensor or the like, the amount of exercise done by the user can be estimated from information such as the number of steps.

Specifically, since it is unknown how much load of exercise is needed and how long it should be done in order to use the energy of x kcal, some information needs to be referred to. Also, the same degree of energy use can be achieved within a shorter time with a high-load exercise. However, a low-load exercise needs to be continued for a longer time than the high-load exercise. In short, if there is no proper guide, the degree of exercise load to be taken is up to the user's decision. Therefore, there is a possibility that user may do an excessively high-load exercise and consequently get injured or result in poor physical condition. Also, while it is known that fat burning efficiency varies depending on the exercise load, there is a possibility that the user may do an exercise with a load that is inefficient for fat burning. In such a case, a sufficient health maintenance or enhancement effect cannot be achieved to the user's effort. Moreover, it is highly likely that a user who has decided to do a high-load exercise or a user who thinks he/she is doing a proper exercise but cannot achieve efficient weight loss, or the like, becomes less motivated to use the service. Consequently, as the user does not use the service continuously, it is difficult to achieve the purpose of the service, that is, maintenance and enhancement of health.

Thus, the present applicant proposes a technique which enables a user to easily set, by himself/herself, a target of health enhancement that matches the aim and lifestyle of the user. More specifically, the present applicant proposes a technique in which target setting is flexibly carried out by flexibly changing a value involved in target setting, such as a zone staying time (in a broad sense, staying time information), that is, a period for which the user caries out an exercise within a proper intensity range. Here, a zone staying time is found on the basis of pulse wave information and body movement information of the user. For example, if the pulse rate is acquired as pulse wave information, a predetermined numerical range of the pulse rate can be defined as a fat burning zone, and the time during which the pulse rate of the user is within the fat burning zone can be defined as a zone staying time. The value of the pulse rate is correlated with the exercise state of the user. Generally, the pulse rate becomes higher as the exercise load becomes higher. That is, in the case where a standard value of the zone staying time is presented as information involved in target setting, the user can be prevented from doing a high-load exercise that may require a pulse rate above the fat burning zone. Also, if an efficient numerical range for fat burning is set literally as a fat burning zone, achieving a predetermined zone staying time is equivalent to executing an exercise that can efficiently burn fat for predetermined time, and therefore the foregoing problems can be solved.

Also, in addition to the staying time information (period for which a proper exercise is carried out), when the user changes information about target body weight and target body fat, information about a period to achieve the target, and the like, depending on the target achieving status, physical condition, mood or the like, Moreover, if a technique such as displaying the present pulse rate along with the numerical range of the fat burning zone or displaying information about whether the present pulse rate is below the lower limit of the fat burning zone, within the zone, or above the upper limit of the zone, with an icon or the like, is used, the user can easily adjust the exercise load, viewing the display. Specifically, if the pulse rate is below the zone, measures such as raising the running pace can be taken to increase the exercise load. If the pulse rate is above the zone, the exercise load can be decreased. That is, using the concept of the fat burning zone and the zone staying time, the user can make adjustments more easily than in the case where an instruction such as "Do exercise equivalent to XX kcal" is given.

Hereinafter, an example of the system configuration of an information processing system or the like which generates a target value on the basis of information involved in target calculation such as staying time information will be explained. Subsequently, with reference to the drawings, it will be explained that staying time information is a proper indicator value in the technique in which the user flexibly carries out target setting by himself/herself, as a principle of the invention, and a relational expression between staying time information and body weight fluctuation will be defined. Then, specific target information generation processing using this relational expression will be explained.

2. Examples of System Configuration

FIG. 1 illustrates an example of a data flow in the technique of this embodiment. The subjects in FIG. 1 represent users who carry out activities aiming at maintenance and enhancement of health. The users acquire necessary information (described in detail below) for target setting when carrying out an exercise, from an information processing system, and create an exercise plan based on the information. Here, the mentor may play the role of an advisor for the subjects, giving the subjects proper advice. In such a case, the subjects may directly refer to advice information generated by the information processing system. The example of FIG. 1 includes a configuration in which advice information is first outputted to the mentor, and in which the mentor gives advice to each subject on the basis of the advice information.

As shown in FIG. 1, a platform 10 includes an operations management service 11, a pulse device connection interface 12, a platform main body 13, a shared database 14, and an advice engine 15. For example, the whole of the platform 10 corresponds to the information processing system of this embodiment.

The operations management service 11 serves as an interface between the platform 10 and the subject or the mentor, and accepts biological information such as pulse wave information, information about diet, body information, target information or the like from the subject. Also, the operations management service 11 has a relay function for transmitting necessary information for target setting, from the platform to the user. Moreover, the operations management service 11 accepts a request for data of a specific subject or specific advice information, from the mentor, and sends information back in response to the request.

The pulse device connection interface 12 is an interface which connects a pulse device (in a narrow sense, a pulsimeter) worn by the subject. Pulse wave information may be acquired from the pulse device connected to the pulse device connection interface 12. However, a configuration in which the device is not directly connected is also highly conceivable, as in the case where the platform 10 is realized as a server system. Also, the pulse device connection interface 12 and the operations management service 11 may be integrated. Alternatively, the pulse device connection interface 12 may be provided on the side of the user (subject or mentor).

The platform main body 13 is connected to each of the other parts of the platform 10, and requests acquisition or output of information, information management, or predetermined processing, and carries out acquisition of a response to the request, or the like.

The shared database 14 stores various kinds of information including individual information such as sex, age and height of the users, and pulse wave information, body information, and target information, as shown in FIG. 1.

The advice engine 15 generates advice information when a request for advice to a specific user is made. The processing by the advice engine not only uses information that is obtained at present but also uses future prediction information estimated from the present information.

In the example of FIG. 1, first, a subject periodically transmits information such as pulse wave information to the platform 10, using the operations management service 11 as an interface. Then, if there is a need to give advice to the subject, the mentor in charge of the subject requests advice for the subject (XXX) from the platform 10, using the operations management service 11 as an interface.

The platform main body 13 accepts the request by the mentor and request advice information for XXX from the advice engine 15. The advice engine 15 acquires data about XXXX from the shared database 14 in order to generate advice information for XXX. The advice engine 15 carries out prediction processing based on the data of XXX. The prediction processing, which will be described in detail later, is processing using the following equation (3) or the like, for example.

The advice engine 15 generates advice information based on the data of XXX and prediction information. The generated advice information is transmitted to the mentor via the platform main body 13 and the operations management service 11.

The mentor gives advice to the subject (XXX) on the basis of the advice information that is sent back as a response to the request for advice. How the advice information is used for the actual advice is left to the mentor's discretion. However, in this embodiment, since proper advice information is generated using the zone staying time, it is expected that there is not much modification work or the like done by the mentor. Therefore, it is possible to reduce the effort of the mentor required for advice or to restrain discrepancies or the like about advice between mentors according to the skill levels of the mentors.

Next, an example of the configuration of an information processing system 100 will be described with reference to FIG. 2.

Figure 2:
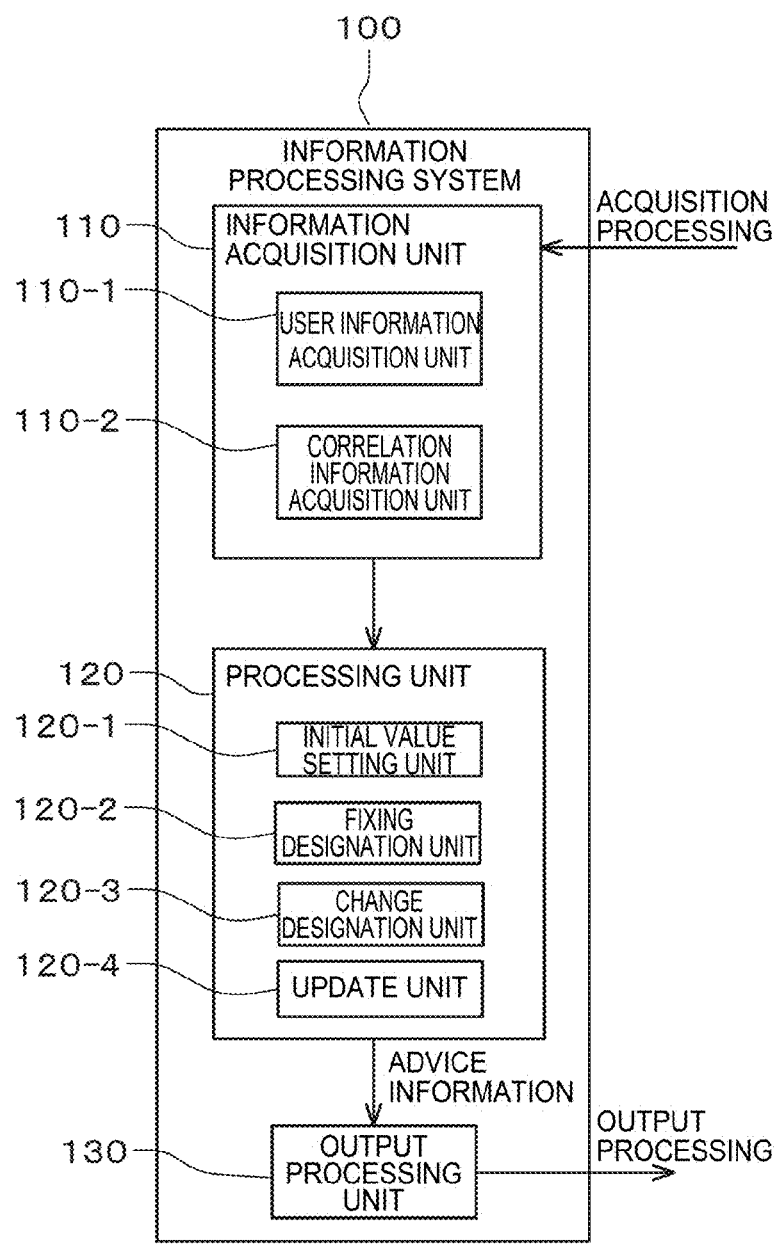
FIG. 2 shows an example of the configuration of an information processing system according to the embodiment.

FIG. 2 shows an example of the configuration of the information processing system 100 of this embodiment. As shown in FIG. 2, the information processing system 100 includes an information acquisition unit 110, a processing unit 120, and an output processing unit 130. However, the information processing system is not limited to the configuration of FIG. 2 and can be modified in various manners such as omitting a part of the components or adding another component. This point that the configuration can be modified in various manners also applies to FIG. 3 and the like.

Figure 3:
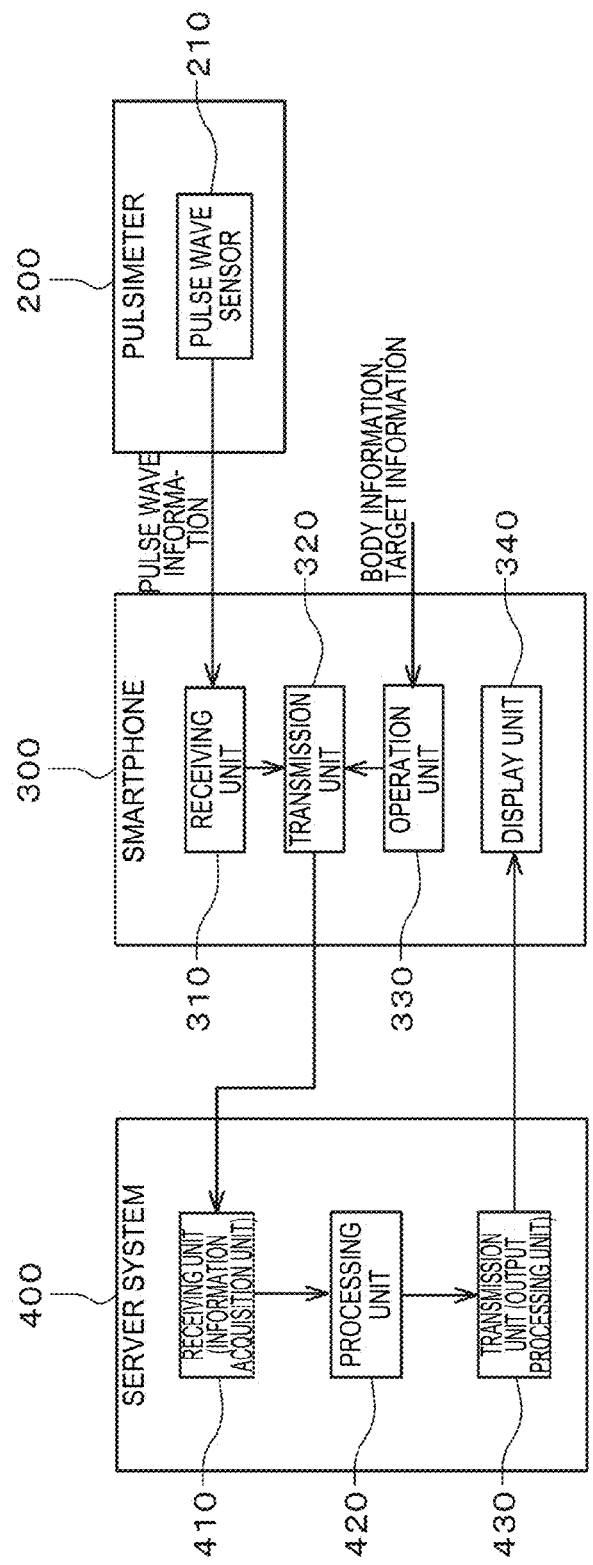
FIG. 3 shows an example of the configuration in the case where the information processing system is realized as a server system.

The information acquisition unit 110 carries out acquisition processing to acquire various kinds of information. Here, the various kinds of information refer to staying time information representing the time during which the value of pulse rate is a value within the fat burning zone (that is, information about the period during which an exercise is carried out within a proper intensity range), body information about the body weight or the body fat mass or the like of the user, target information about the weight loss of the user, and the like. As will be described later with reference to FIGS. 3 and 4, the information processing system of this embodiment can be realized in various forms. Therefore, the specific content of the information acquisition processing may vary depending on embodiments. The acquisition processing by the information acquisition unit 110 may be, for example, reception processing via a network or the like as shown in FIG. 3, or reception processing to receive an information input via an interface, as shown in the form of an operation unit 353 in FIG. 4.

The information acquisition unit 110 includes a user information acquisition unit 110-1 and a correlation information acquisition unit 110-2. The user information acquisition unit 110-1 acquires first information, second information, and third information about the user. The correlation information acquisition unit 110-2 acquires correlation information representing the relation between the first information, the second information, and the third information. Each of the first information, the second information and the third information may be one of the body information, the exercise information, and the target information of the user, and that is different from each other. According to this, target setting in which a value involved in target calculation such as a decision on a target value (exercise information) based on the target information and the body information is flexibly changed, can be realized. The correlation information acquisition unit 110-2 may acquire correlation information by reception processing via a network or the like. According to this, a user-friendly user interface which acquires correlation information from a communication unit can be provided. Moreover, the user information acquisition unit 110-1 may acquire the first information, the second information, and the third information of the past, present, or future. According to this, since the first information, the second information, and the third information of the past, present, or future are acquired, the target can be made visible.

The processing unit 120 generates advice information based on the information acquired by the information acquisition unit 110 and a relational expression. The relational expression in this case is an equation that associates the zone staying time and the fluctuation in body weight (or the fluctuation in body fat mass), as will be described in detail later.

The processing unit 120 includes an initial value setting unit 120-1, a fixing designation unit 120-2, a change designation unit 120-3, and an update unit 120-4. The initial value setting unit 120-1 sets initial values of the first information, the second information, and the third information. The fixing designation unit 120-2 designates fixing of the first information. The change designation unit 120-3 designates change of the second information. The update unit 120-4 updates the third information on the basis of the correlation information. The initial value setting unit 120-1 may set initial values of the first information, the second information, and the third information on the basis of the body information of the user. According to this, assistance can be provided in reasonable and effective target setting in which an achievable target for the user is set.

The output processing unit 130 carries out output processing to output the advice information generated by the processing unit 120. Similar to the acquisition processing by the information acquisition unit 110, the output processing by the output processing unit 130 can be realized in various forms. For example, the output processing may be transmission processing via a network or the like as shown in FIG. 3, or processing to perform display control on a display unit 380, as shown in the form of a display control unit 370 in FIG. 4. The display unit 380 may display the result of the designation by at least one of the fixing designation unit and the change designation unit, and the third information updated by the update unit. The advice information may be displayed by a graphic display method. According to this, a user-friendly user interface which visually presents information to the user with a chart can be provided.

Next, a specific example of realization of the information processing system will be described with reference to FIGS. 3 and 4. The example of realization of the information processing system is not limited to FIGS. 3 and 4 and can be modified in various manners.

FIG. 3 shows an example of the configuration in the case where the information processing system 100 is realized as a server system 400. In the example of FIG. 3, the subject wears a pulsimeter 200 and carries a smartphone 300. A pulse wave sensor 210 included in the pulsimeter 200 transmits pulse wave information to a receiving unit 310 of the smartphone 300. An operation unit 330 of the smartphone 300 accepts an input of body information and target information from the subject. A transmission unit 320 of the smartphone 300 transmits the pulse wave information, the body information, the target information or the like to the server system 400.

A receiving unit 410 of the server system 400 receives the pulse wave information or the like transmitted thereto. A processing unit 420 processes the information received by the receiving unit 410 and thus generates advice information. The generated advice information is transmitted from a transmission unit 430 of the server system 400 to the smartphone 300 and displayed on a display unit 340 of the smartphone 300. The receiving unit 410 includes a user information acquisition unit and a correlation information acquisition unit (not shown), similarly to the information acquisition unit 110 shown in FIG. 2. Details of these units are omitted. The processing unit 420 includes an initial value setting unit, a fixing designation unit, a change designation unit, and an update unit (not shown), similarly to the processing unit 120 shown in FIG. 2. Details of these units are omitted.

That is, in the example of FIG. 3, the receiving unit 410 corresponds to the information acquisition unit 110. The processing unit 420 corresponds to the processing unit 120. The transmission unit 430 corresponds to the output processing unit 130. In FIG. 3, as the subject carries the smartphone 300, advice information is provided to the subject without the mentor. In this respect, the example of FIG. 3 is different from the example of FIG. 1.

Figure 4:
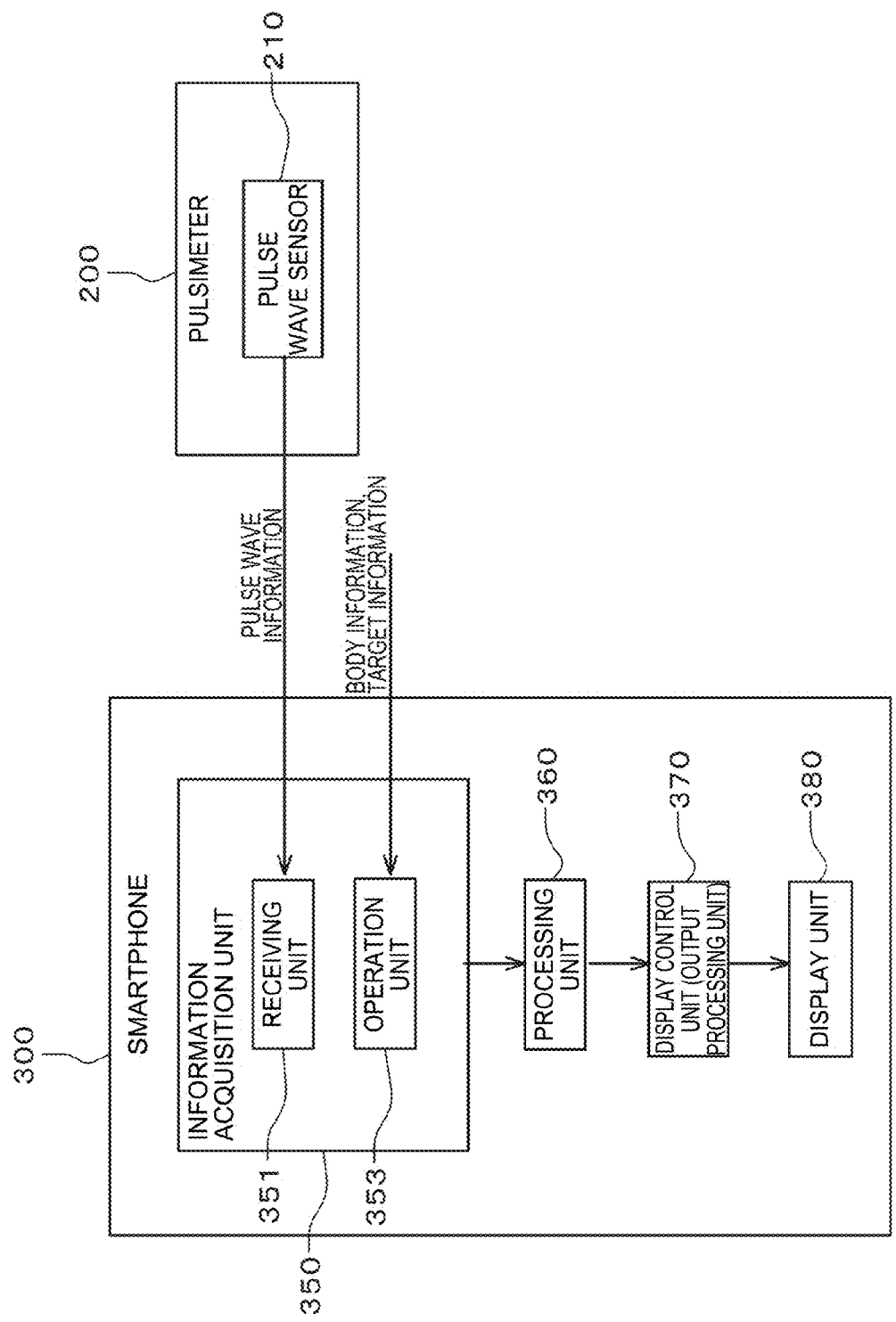
FIG. 4 shows an example of the configuration in the case where the information processing system is realized as a smartphone.

FIG. 4 shows an example of the configuration in the case where the information processing system 100 is realized as the smartphone 300. In the example of FIG. 4, the subject wears a pulsimeter 200 and carries the smartphone 300. A pulse wave sensor 210 included in the pulsimeter 200 transmits pulse wave information to a receiving unit 351 included in an information acquisition unit 350 of the smartphone 300. An operation unit 353 included in the information acquisition unit 350 of the smartphone 300 accepts an input of body information and target information from the subject. The information acquisition unit 350 includes a user information acquisition unit and a correlation information acquisition unit (not shown), similarly to the information acquisition unit 110 shown in FIG. 2. Details of these units are omitted.

A processing unit 360 processes the information acquired by the information acquisition unit 350 and thus generates advice information. A display control unit 370 performs display control of the advice information. A display unit 380 displays the advice information under the control of the display control unit 370. The processing unit 360 includes an initial value setting unit, a fixing designation unit, a change designation unit, and an update unit (not shown), similarly to the processing unit 120 shown in FIG. 2. Details of these units are omitted.

That is, in the example of FIG. 4, the information acquisition unit 350 including the receiving unit 351 and the operation unit 353 corresponds to the information acquisition unit 110 of FIG. 2. The processing unit 360 corresponds to the processing unit 120. The display control unit 370 corresponds to the output processing unit 130.

In the above description, it is assumed that the output from the pulsimeter 200 is pulse wave information. In this case, it is conceivable that the processing to find staying time information on the basis of the pulse wave information is carried out in a block corresponding to the information acquisition unit 110, in the smartphone 300 or the server system 400. However, in this embodiment, such a configuration is not limiting and arithmetic processing to find staying time information may be carried out in the pulsimeter 200. In such a case, staying time information is found by the firmware or the like of the pulsimeter 200 on the basis of the pulse wave information from the pulse wave sensor 210, and the resulting staying time information is outputted to the smartphone 300 or the like.

3. Relational Expression Between Zone Staying Time and Body Weight Fluctuation

As described above, in the embodiment, advice information is created on the basis of a zone staying time that is a time during which the value of pulse rate or the like is in the fat burning zone. Specifically, a relational expression which associates the fluctuation in body weight or the fluctuation in body fat mass and the zone staying time is found, and advice information is created using the relational expression. Hereinafter, a relational expression will be derived using FIG. 5 or the like, and the validity of the relational expression will be explained.

Figure 5:
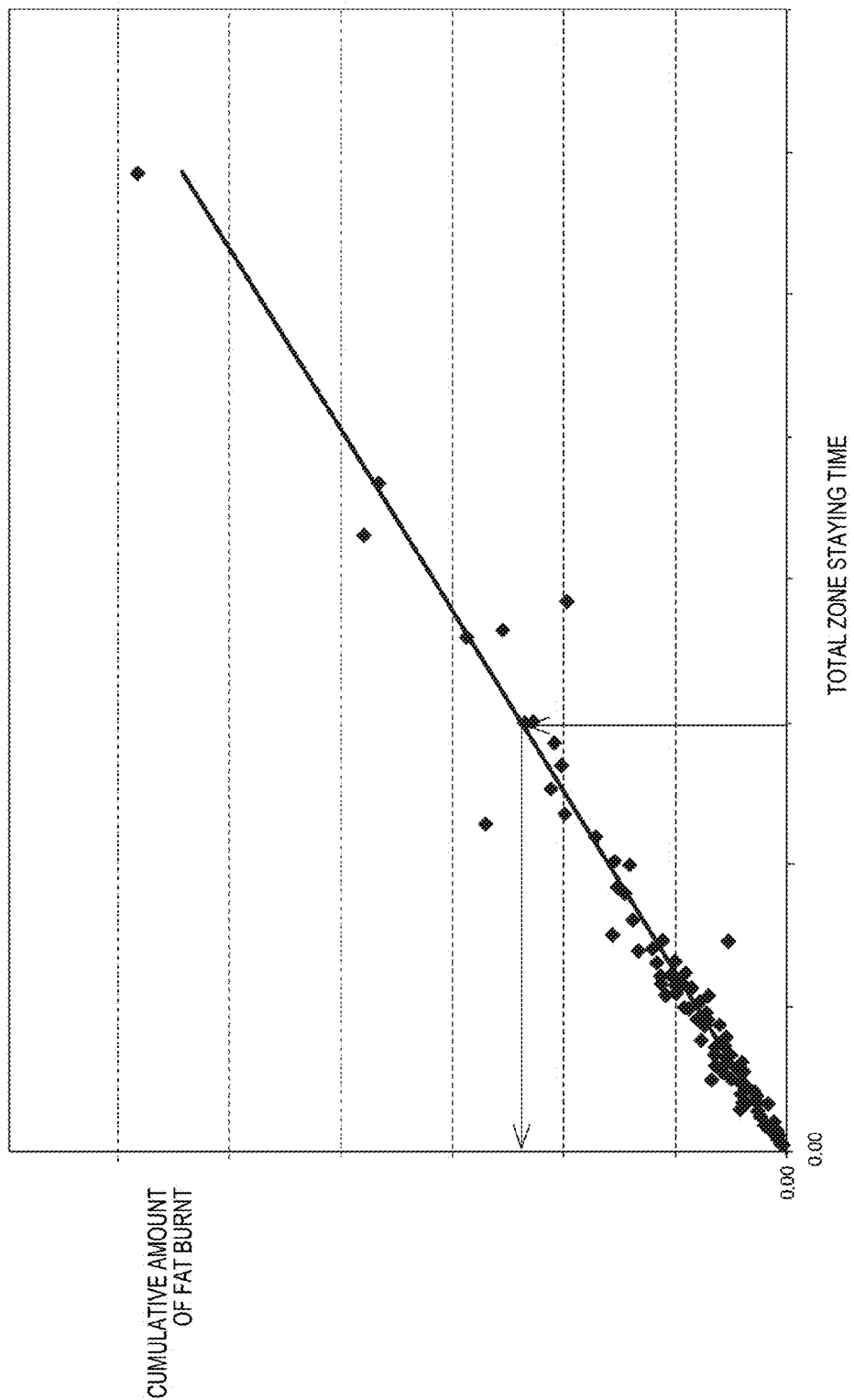
FIG. 5 shows the relation between the cumulative value of zone staying time and the cumulative value of amount of fat burned.

FIG. 5 shows the relation between the cumulative value of the zone staying time and the cumulative value of the amount of fat burned. Specifically, FIG. 5 is a chart plotting actually measured values obtained from user data, with the horizontal axis representing the cumulative value of the zone staying time and the vertical axis representing the cumulative value of the amount of fat burned.

As clear from FIG. 5, the cumulative value of the zone staying time and the cumulative value of the amount of fat burned have a strong correlation. As shown in FIG. 5, the plotted points are distributed around a regression line, and the resulting correlation coefficient is a value that is close to 1.

That is, from the analysis of FIG. 5 using actually measured values, it can be learned that the zone staying time and the amount of fat burned have a strong correlation. In FIG. 5, since correction processing based on the age, sex, body weight and the like of the user is not carried out, there are variations due to those factors. However, the correlation is sufficiently strong, even when such variation factors are taken into account. As a result, a prediction that "if the subject exercises for x hours so that the pulse rate reaches a value within the fat burning zone, the subject can lose a maximum of y kg of body fat" can be made. In this case, age, sex, body weight and the like need not be considered.

However, the values on the vertical axis in FIG. 5 are based on the assumption that all of the expended calories are used to burn fat and the assumption that the amount of fat burned is equal to the actual amount of body fat lost. However, in practice, it is known that, of all the expended calories, only a part of the energy is used to burn fat. Also, it is very likely that the amount of fat burned is not equal to the amount of body fat lost, considering the calorie intake from meals or the like. That is, if the above prediction is described more accurately, it will be that if the subject exercises for x hours so that the pulse rate reaches a value within the fat burning zone, "ideally" the subject can lose a maximum of y kg of body fat.

In the embodiment, since the advice information is specifically information about weight loss, the advice information needs to be based on a realistic amount of body weight lost or body fat lost, instead of an ideal amount of fat burned. That is, to derive the relation between the zone staying time and the amount of body weight lost or body fat lost, the analysis shown in FIG. 5 alone is insufficient.

Next, the relation between the rate of the zone staying time per unit time (hereinafter also referred to as a zone staying rate) and the amount of fat burned per unit time will be explained.

Figure 6:
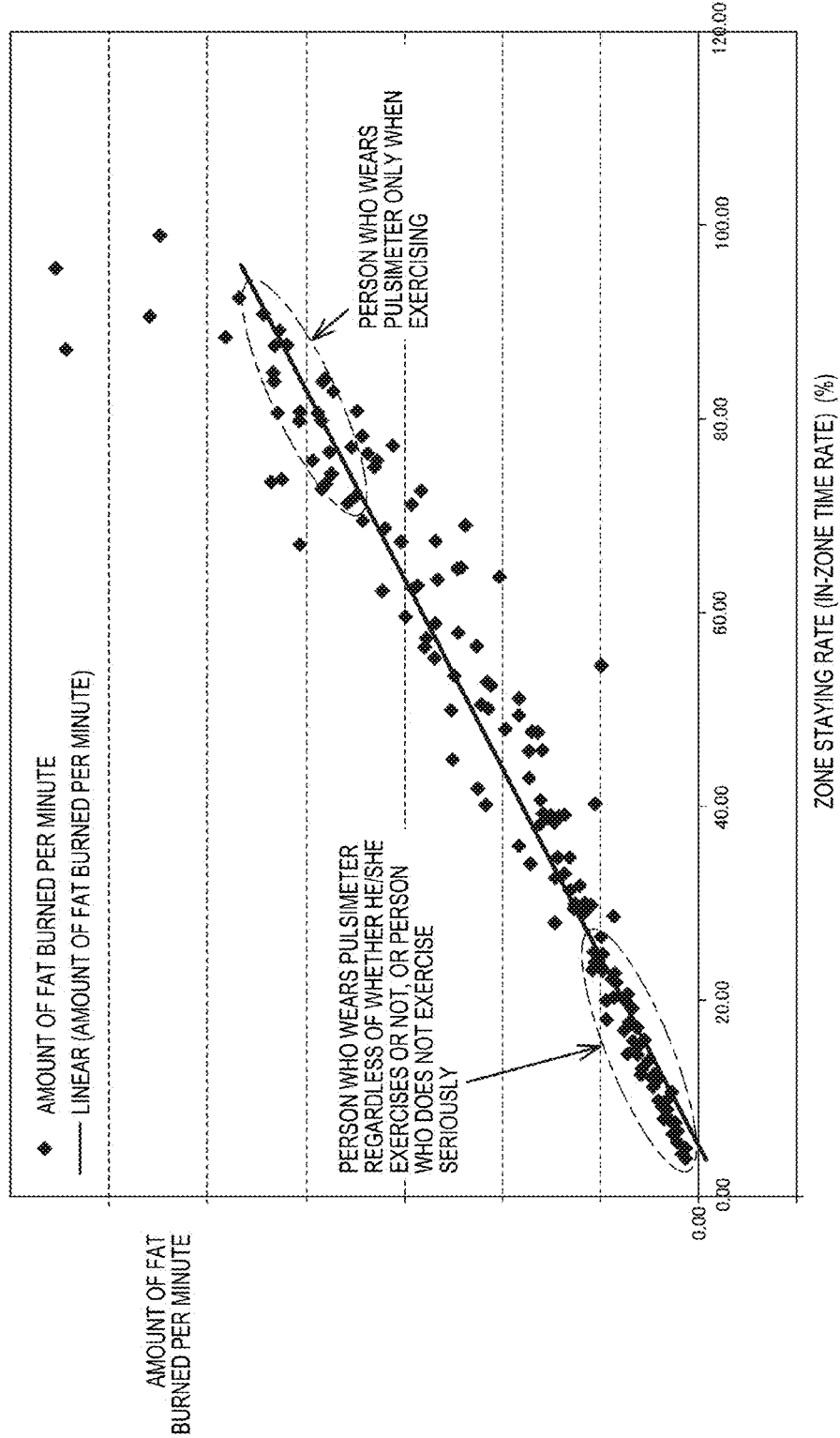
FIG. 6 shows the relation between zone staying rate and amount of fat burned per unit time.

FIG. 6 shows the relation between the zone staying rate and the amount of fat burned per unit time. The horizontal axis represents the percentage of the length of the zone staying time, for example, during an hour. More specifically, values on the horizontal axis are 100% if the pulse rate is a value within the fat burning zone constantly (for 60 minutes) during an hour, and 50% if the pulse rate is within the fat burning zone for 30 minutes and out of the fat burning zone for the remaining 30 minutes.

As the horizontal axis is thus defined, the position of distributed points in the graph varies depending on the wearing status of the pulsimeter and the user's commitment to the exercise. For example, a user with a value close to 100% on the horizontal value is a user who wears the pulsimeter only in exercising states, that is, only when the pulse rate is higher than the normal value and reaches a value within the fat burning zone, and who is vigorously committed to exercising. Meanwhile, a user with a value close to 0% on the horizontal axis is a user who wears the pulsimeter at other times than when exercising, or a user who wears the pulsimeter only in exercising states but who has insufficient exercise load by not being vigorously committed to exercising or the like. That is, by viewing values on the horizontal axis, it is possible to learn the pulsimeter wearing status, the exercising status and the like, for each user.

That is, on the basis of the analysis using FIG. 6, it can be understood that not only the cumulative value of the zone staying time as shown in FIG. 5 but also the zone staying rate has a strong correlation with the amount of fat burned. In other words, it can be understood that the zone staying rate can be used as an indicator value, regardless of the pulsimeter wearing status and the exercising status of each user. Also, since the use of the zone staying rate as an indicator value enables estimation of the pulsimeter wearing status and the exercising status of each user as described above, it is possible to generate advice information corresponding to these statuses.

However, also in FIG. 6, since the vertical axis represents the amount of fat burned, the conclusion that the amount of body fat lost can be decided on the basis of the zone staying rate cannot be reached without further considering the relation with the actual amount of body fat lost, as in the case of FIG. 5.

Next, the relation between the zone staying rate and the amount of fat burned per unit time, and the relation between the zone staying rate and the amount of body fat lost per unit time will be described.

Figure 7:
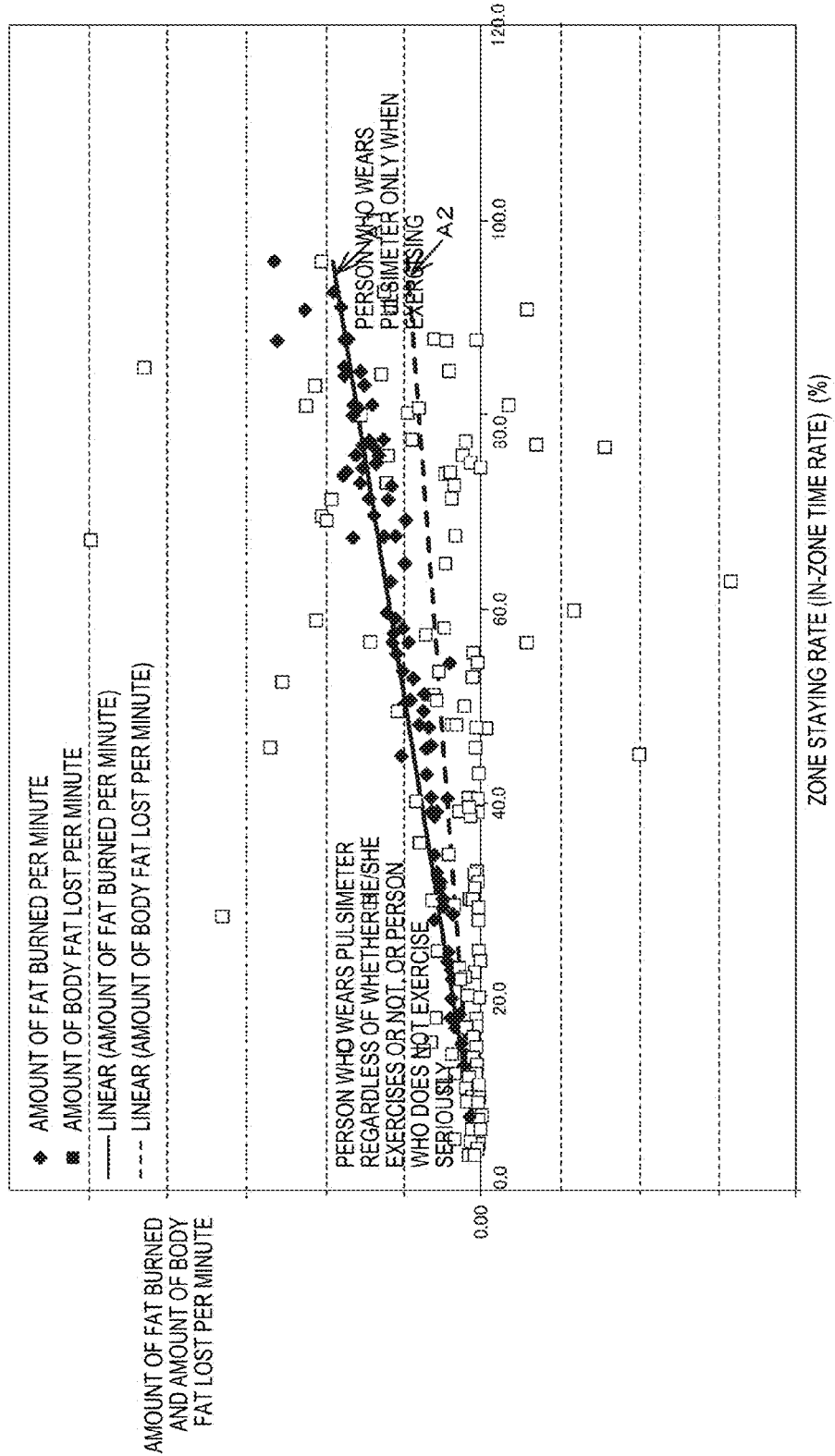
FIG. 7 shows the relation between zone staying rate and amount of fat burned per unit time, and the relation between zone staying rate and amount of body fat lost per unit time.

FIG. 7 shows the relation between the zone staying rate and the amount of fat burned per unit time, and the relation between the zone staying rate and the amount of body fat lost per unit time. The relation between the zone staying rate and the amount of fat burned per unit time is similar to that of FIG. 6, and it can be understood that there is a strong correlation between the two.

The relation between the zone staying rate and the amount of body fat lost per unit time has very large variations because calorie intake is not considered. Also, the correlation coefficient is a small value. However, since the statistical significance level is 0.3%, the correlation between the zone staying rate and the amount of body fat lost cannot be dismissed even though it is a weak correlation. That is, even if only the relation between the zone staying rate and the amount of body fat lost per unit time is considered, the result of the analysis is that there is a correlation between the two that cannot be dismissed.

Also, it is possible to conduct an analysis using both a regression line A1 found from the distribution of the zone staying rate and the amount of fat burned per unit time and a regression line A2 found from the distribution of the zone staying rate and the amount of body fat lost per unit time. Since there is a strong correlation between the zone staying rate and the amount of fat burned, as described above, the regression line A1 is highly reliable. Also, it is found that if the regression line A2 is found from actually measured values, the slope of the regression line A2 is approximately ½ of the slope of the regression line A1. Here, the theory that approximately ½ of expended calories is generally used to burn fat, is broadly known. The amount of fat burned, which is one of the amounts expressed on the vertical axis, shows the value on the assumption that all the expended calories are used to burn fat, as described above. Therefore, if the expended calories used to burn fat are approximately ½ of all the calories, the actually burned fat, that is, the amount of body fat lost should be ½ of the amount of fat burned in FIG. 6. That is, considering that the regression line A1 is a regression line of an ideal amount of fat burned (corresponding to all the expended calories), that it is known that theoretically the amount of body fat lost is ½ of the regression line A1, and that the slope of the regression line A2 found from the amount of body fat lost that is actually measured is ½ of the slope of the regression line A1, it is possible to derive a conclusion that the regression line A2 conforms to the theory as a relational expression that expresses the amount of body fat lost.

In short, the analysis using FIG. 7 can lead to a result that the regression line A2 is appropriate as a relational expression expressing the relation between the zone staying rate and the amount of body fat lost. Considering that there is a strong correlation between the two both in FIGS. 5 and 6, it is possible to conclude that, if a regression line with respect to the zone staying rate and the amount of body fat lost is found, this regression line is a proper relation expression that decides the relation between the zone staying rate and the amount of body fat lost.

Based on the above, if the amount of body fat lost (in a broad sense, an amount of fluctuation) is W, the zone staying rate is T_zone, and the coefficient decided by the regression line (for example, a value decided by the slope: fat burning coefficient) is Kfat, the relation between these elements is decided by the equation (1).

$$T\_zone \times Kfat = W \quad (1)$$

According to this, the staying time information and the fluctuation in body weight or the like can be associated with each other, using the above relational expression.

Next, the relation between the amount of body fat lost and the amount of body weight lost will be described.

Figure 8:
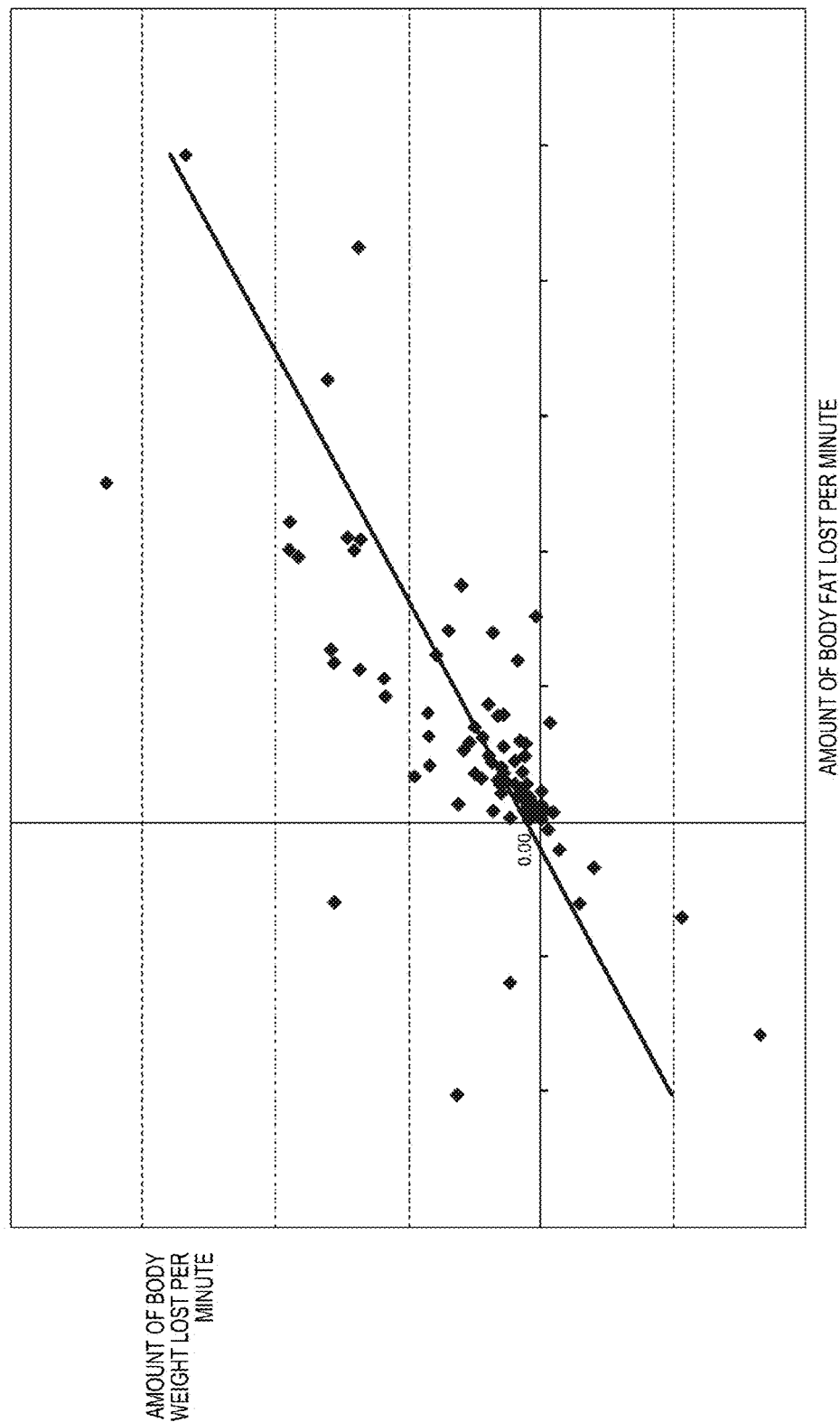
FIG. 8 shows the relation between amount of body fat loss and amount of body weight loss.

FIG. 8 shows the relation between the amount of body fat lost and the amount of body weight lost. Specifically, FIG. 8 is a chart plotting actually measured values obtained from users, with the horizontal axis representing the amount of body fat lost, and the vertical axis representing the amount of body weight lost. Here, the slope of the regression line shown in FIG. 8 is approximately 1. That is, the analysis using FIG. 8 can lead to a conclusion that the amount of body fat lost and the amount of body weight lost can be equated with each other.

The value of body weight can be measured with a widely available body weight scale and is known to have a relatively small error. In contrast, body fat mass cannot be measured without using a body weight scale or the like having the function of a body fat meter, and even if body fat mass (or body fat percentage) can be measured, its value has a large error, compared with the measured value of body weight. In short, it is highly likely that the information about the body fat mass of the user is not inputted or is inputted inaccurately. That is, while the description using FIGS. 5 to 7 and the equation (1) is limited to body fat mass, body fat mass may replace body weight, considering the result of the analysis using FIG. 8. Specifically, it is possible to carry out prediction processing, using W in the equation (1) as the amount of fluctuation in body weight.

4. Specific Example of Processing Using Relational Expression

Next, a technique for generating advice information, that is, information about change in body weight corresponding to a period during which an exercise is done within a proper intensity range, by actually using the relational expression of the equation (1), will be described. Specifically, processing at the start of an advice period and processing at an advice timing that is a predetermined timing during the advice period will be described.

The advice period in this case corresponds to a period during which the user (subject) receives the provision of a service using the information processing system of this embodiment. For example, the start point of the advice period may be the timing when the user orders the service or may be the timing when transmission of pulse wave information or the like is actually started. If a service use period is set when the service is ordered, the end point of the advice period may be the timing when the use period passes from the start point of the advice period. Also, the end point of the advice period may be changed suitably according to an application or the like by the user. The service referred to in this case includes applications or the like that operates on electronic apparatuses such as a smartphone, tablet, personal computer and game machine, as well as onerous and gratuitous health enhancement services provided by corporations and enterprises. When using such an application, the user can arbitrarily decide the service period and the start and end points of the advice period.

The start point of the advice period may be decided at the point when data analysis is started, instead of at the start of the use of the service. For example, there is a case where a user orders the use of a service for six months but cannot take time for exercise during the first three months for personal reasons. In this case, even if the user exercises sufficiently in the latter three months, it can be determined that the exercise is insufficient as a whole, due to the data of the first three month. To cope with this situation, the user can reset the start point of the advice period to the point of three months after the use of the service is started.

However, in the similar case, instead of resetting the advice period, it is also conceivable that there are two data totaling periods ($0^{th}$ to third month, and third to sixth month) during the advice period, while the advice period is started when the use of the service is started. That is, the advice period in this embodiment is a concept that includes both the case where the advice period is set on the basis of the start of the use of the service and the case where the advice period is set on the basis of the data totaling period. In the description below, an example of the advice period based on the start of the use of the service will be described.

4.1 Processing at Start of Advice Period (Target Setting Processing)

First, target setting processing carried out at the start of the advice period will be described. Specifically, this processing is to accept an input of body information and target information from the subject or the mentor and find staying time information required to achieve the target information. The staying time information may be the cumulative value of the zone staying time or may be the zone staying rate. However, in this example, the zone staying time per day is used. Also, while either body weight or body fat mass can be used as described above, body weight is used as an example in the description below.

As the body information, the present body weight $W_{ini}$ of the user (present value of body weight) is acquired. As the target information, a target body weight $W_{target}$ of the user (target value of body weight) and a target period $T_{target}$ (days) that is a period for achieving the target body weight are acquired.

In this case, if T_zone represents the zone staying time per day, the equation (1) can be modified into the equation (2) and consequently T_zone can be found by the equation (3). In the equations (2) and (3), since the amount of body weight lost is a positive value, the target value is subtracted from the present value of body weight on the right side.

$$T\_zone \times T_{target} \times Kfat = W_{ini} - W_{target} \quad (2)$$

$$T\_zone = (W_{ini} - W_{target})/(T_{target} \times Kfat) \quad (3)$$

Here, $W_{ini}$, $W_{target}$ and $T_{target}$ on the right side of the equation (3) are already found by the information acquisition unit 110 on the basis of the statistics shown in FIG. 7 or the like, as described above. That is, by applying the acquired information to the equation (3), the zone staying time per unit required to achieve the target body weight in the target period can be found as T_zone.

Now, processing to change the zone staying time per day, the target body weight and the target period, carried out by the user, will be described. That is, in the information processing system 100, one of the parameters of the zone staying time, the target body weight and the target period can be fixed, another one can be changed by the user, and the remaining one can be automatically changed through calculation (table) by the system.

The processing unit 120 generates fixing designation information to designate fixing of one of the three kinds of information of the zone staying time, the target body weight and the target period. For example, the processing unit 120 generates fixing designation information to designate fixing of the target body weight. The processing unit 120 generates modification designation information to designate modification of one of the remaining two. For example, the processing unit 120 generates modification designation information to designate modification of the zone staying time, of the zone staying time and the target period. Based on the fixed one of the three kinds of information and the modified one of the remaining two of the three kinds of information, the processing unit 120 carries out processing to find the other information of the remaining two again. For example, the processing unit 120 finds the target period again on the basis of the fixed target body weight and the modified zone staying time.

The information acquisition unit 110 carries out acquisition processing to acquire the one that is fixed on the basis of the fixing designation information generated by the processing unit 120, of the three kinds of information of the zone staying time, the target value and the target period. For example, the information acquisition unit 110 carries out acquisition processing to acquire the target body weight fixed on the basis of the fixing designation information generated by the processing unit 120. The information acquisition unit 110 carries out acquisition processing to acquire the one of the remaining two that is modified on the basis of the modification designation information generated by the processing unit 120. For example, the information acquisition unit 110 carries out acquisition processing to acquire the zone staying time modified on the basis of the modification designation information generated by the processing unit 120.

Thus, in the information processing system 100, if the target body weight is fixed and the zone staying time per day is changed by the user, the target period is automatically changed. The user can repeat changing the zone staying time per day until the target period reaches a reasonable value.

Next, target setting processing carried out by the user will be described.

Figure 9:
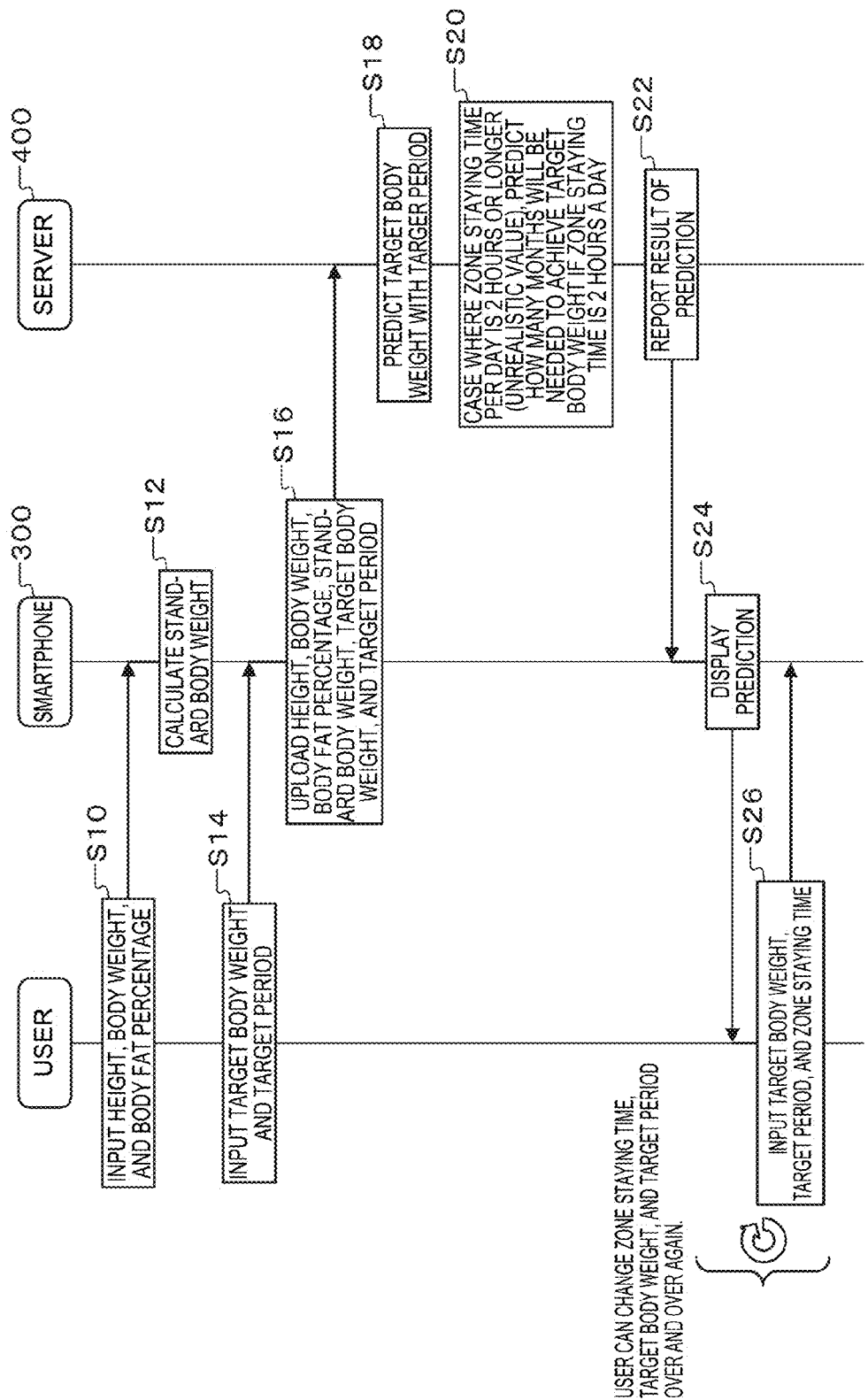
FIG. 9 is a flowchart illustrating target setting processing.

FIG. 9 is a flowchart illustrating the target setting processing. First, in Step S10, the user inputs information (first information) such as height, body weight and body fat percentage to the smartphone 300, as body information.

Next, in Step S12, the smartphone 300 calculates a standard body weight on the basis of the height and body weight.

Subsequently, in Step S14, the user inputs information (second information) such as target body weight and target period to the smartphone 300, as target information.

Next, in Step S16, the smartphone 300 uploads the height, body weight, body fat percentage, standard body weight, target body weight and target period to the server system 400.

Subsequently, in Step S18, the server system 400 derives exercise information (third information) including a prediction on how many hours a day the zone staying time should be to achieve the target body weight in the target period, on the basis of the information uploaded from the smartphone 300, and on the basis of the information acquired in Steps S10 to S14 and the equation (3).

Next, in Step S20, in the case where the zone staying time per day is an unrealistic value, for example, two hours or longer, the server system 400 predicts how many months will be needed to achieve the target body weight if the zone staying time is two hours a day.

Subsequently, in Step S22, the server system 400 reports the result of the prediction to the smartphone 300. At this point, as the result of the prediction reported to the smartphone 300 from the server system 400, the period required to achieve the target, derived in the case where the zone staying time per day is two hours, for example, is provided, and the currently set target body weight, target period, exercise information and the like are displayed on the display unit 340. Referring to these pieces of information, the user can determine whether the target which the user sets himself/herself is appropriate. If the user determines that the current target body weight, target period and exercise information are not appropriate or difficult to achieve, the processing returns to Step S14. Then, the target body weight or target period is modified and information reflecting the modification is received from the server again. Since the user can suitably change necessary conditions while checking to achieve the target that is set by the user himself/herself in this manner, the user can set appropriate target information and exercise information by his or her own decision.

Meanwhile, in Step S24, the result of the prediction provided to the smartphone 300 from the server system 400 may be configured to include a plurality of prediction information. For example, the result of the prediction provided from the server in Step S24 may be a data group, for example, matrix data of 15 rows by 15 columns as shown in FIG. 12, later described, or may be the coordinates and formula or the like at the time of displaying a graph.

In this case, when the target value is modified, there is no need to return to Step S14 to carry out exchanges with the server all over again as described above. If the user determines that the present target body weight, target period and exercise information need to be modified, modification can be made suitably by referring to the data group transmitted from the server in Step S24. Such a configuration dramatically improves operability and responsiveness at the time of target modification. This facilitates target setting that reflects the user's intention. Moreover, since communication is not carried out frequently, waste of power can be prevented.

Figure 10:
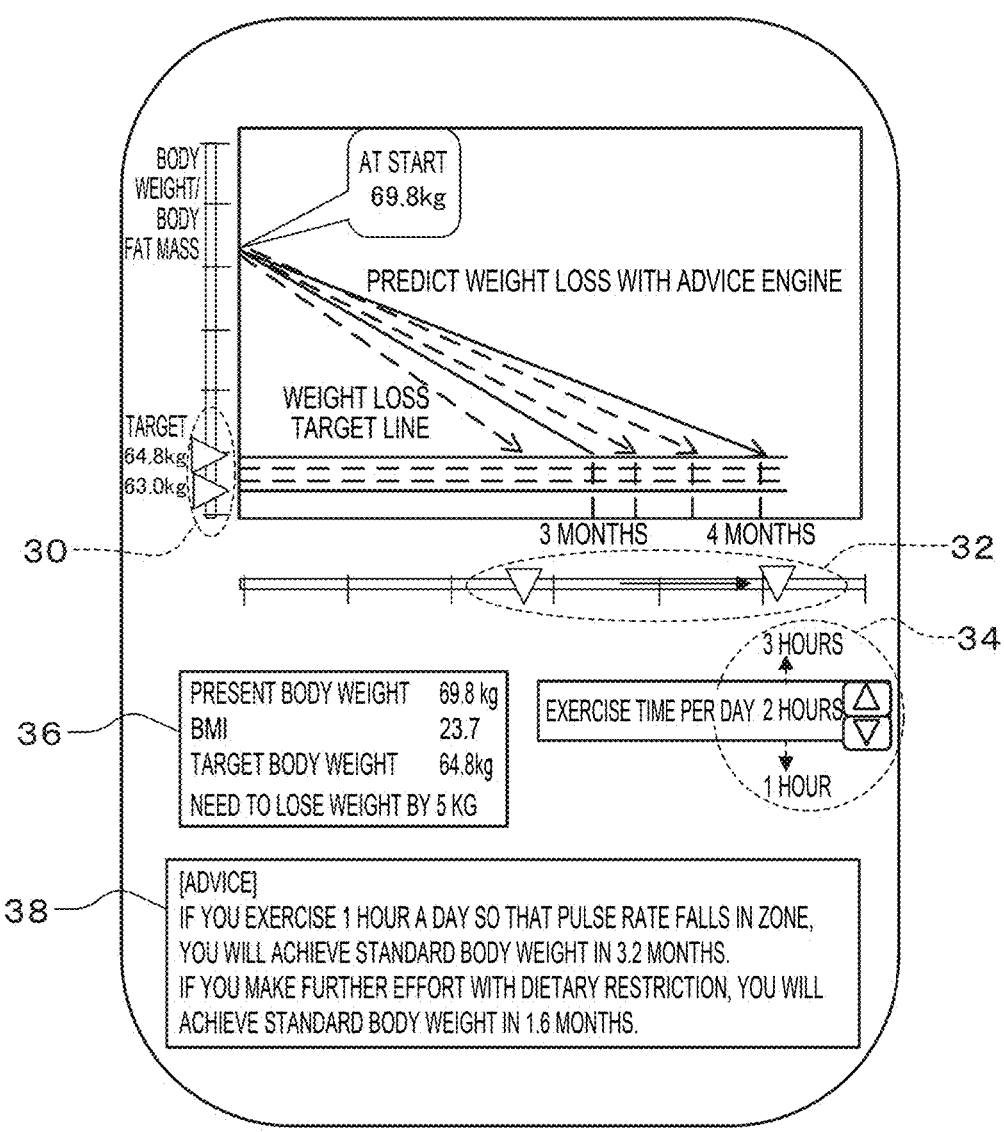
FIG. 10 is another chart illustrating target setting processing.

FIG. 10 is another view illustrating the target setting processing. A weight loss target line which predicts body weight loss is shown in a graph displayed on the display unit 340 of the smartphone 300. The vertical axis represents the body weight/body fat mass, and target body weight. The horizontal axis represents the target period.

An area 30 is an area for changing or fixing the target body weight. An area 32 is an area for changing or fixing the target period. An area 34 is an area for changing or fixing the zone staying time. An area 36 is an area displaying the present status. An area 38 is an area displaying advice information.

For example, the graph of the weight loss target line shown in FIG. 10 shows that the target line, starting at the body weight (present body weight) of 69.8 kg on the vertical axis on the left-hand side, changes in its gradient, depending on each target period. On the body weight/body fat mass scale on the vertical axis, body weight or body fat mass can be selected. The target body weight shown in the area 30 is fixed. Here, it is shown that the target body weight is changed from 63.0 kg and fixed to 64.8 kg. The target period shown in the area 32 may be changed by the user. Here, it is shown that the target period is changed from three months to four months. If the target period is changed by the user, the zone staying time shown in the area 34 is changed with a change in the graph. Here, it is shown that the zone staying time is changed to two hours.

According to this configuration, a user-friendly user interface which visually presents the present setting status to the user with a diagram such as a graph when setting the target value, the target period and the zone staying time, and which allows the user to change the slope of the graph, can be provided.

FIG. 11 shows the relation between the target body weight, the target period, and the zone staying time. In the information processing system 100, in the case where the slope of the graph is automatically changed, the intercept and slope or the coordinates (start point and end point) used to draw the graph may be reported, as well as returning the result of the calculation. When the coordinates are returned, the size of the image needs to be acquired in advance.

Specifically, as shown in FIG. 11, if the user fixes the target body weight (maintains the present set value) and changes the target period, the smartphone 300 calculates and reports the zone staying time. If the user changes the zone staying time, the smartphone 300 calculates and reports the target period, or reports the intercept and slope of the weight loss line, or reports the coordinates (start point and end point).

Also, if the user fixes the target period and changes the target body weight, the smartphone 300 calculates and reports the zone staying time. If the user changes the zone staying time, the smartphone 300 calculates and reports the target body weight, or reports the intercept and slope of the weight loss line, or reports the coordinates (start point and end point).

Moreover, if the user fixes the zone staying time (maintains the present set value) and changes the target body weight, the smartphone 300 calculates and reports the target period, or reports the intercept and slope of the weight loss line, or reports the coordinates (start point and end point). If the user changes the target period, the smartphone 300 calculates and reports the target body weight, or reports the intercept and slope of the weight loss line, or reports the coordinates (start point and end point).

FIG. 12 shows an example of a data group in the case where the result of prediction including a plurality of prediction information is provided from the server system 400. If a person currently weighting 55 kg inputs a target body weight of 50 kg in Step S14, the server system 400 extracts a predetermined range of body weights including the target body weight, as a series of target body weights. Next, with respect to the target period inputted by the user in Step S14, a predetermined period including the value of the target period is extracted as a series of target periods. A table showing the series of target body weights and the series of target periods in rows and columns is created. Then, exercise information corresponding to each target body weight and target period is calculated by the equation (3). The table of prediction information thus created has a data configuration of, for example, 15 rows by 15 columns. Based on the information of FIG. 12, if the target body weight is 50 kg (present value minus 5 kg) and the target period is three months, the zone staying time is 2.7 hours. While the data group of FIG. 12 represents an example of a data configuration directed to achieve a weight loss from the present body weight inputted in Step S14, a configuration including data directed to achieve a weight gain from the present body weight may also be employed. Thus, a proper suggestion on weight gain can be provided to an underweight person.

As an application installed in the smartphone caches the data group of FIG. 12, the graph can be changed without increasing traffic. Also, the possession of the cache function allows the function of changing the graph in real time. Moreover, such functions can be realized without taking processing time for simulation. In the case of the configuration where data as shown in FIG. 12 is received from the server system 400, it is preferable that the smartphone 300 transmits the information inputted by the user in Step 10 (S10) and Step 14 (S14) of FIG. 9, to the server system 400, and that the server system 400 generates data corresponding to FIG. 12 on the basis of these pieces of information. With such a configuration, a flexible target simulation can be realized with minimum necessary data communication.

4.2 Target Resetting Processing

It is conceivable that the target value set by the user at the start of the use of the service may become a different value from the actually measured value with the lapse of time, due to at least one of the calorie intake and the amount of exercise. In such a case, there is a possibility that the initially set value of the zone staying time or the like is no longer appropriate in order to achieve the target value of body weight in the target period.

For example, it is now assumed that, with a target period of six months, the status of progress is checked at the timing of three months after the start. Here, in the case where the target to be achieved in six months is left unchanged and weight loss progresses at a higher pace than the target in the first three months because of reduction in calorie intake or increase in the amount of exercise or the like, the target can be achieved even if the pace of weight loss is lowered by relatively increasing calorie intake or reducing the amount of exercise. On the other hand, in the case where the pace of weight loss is low in the former half of the period, the target body weight cannot be achieved in six months' time even if the user keeps the initially set zone staying time.

Figure 13:
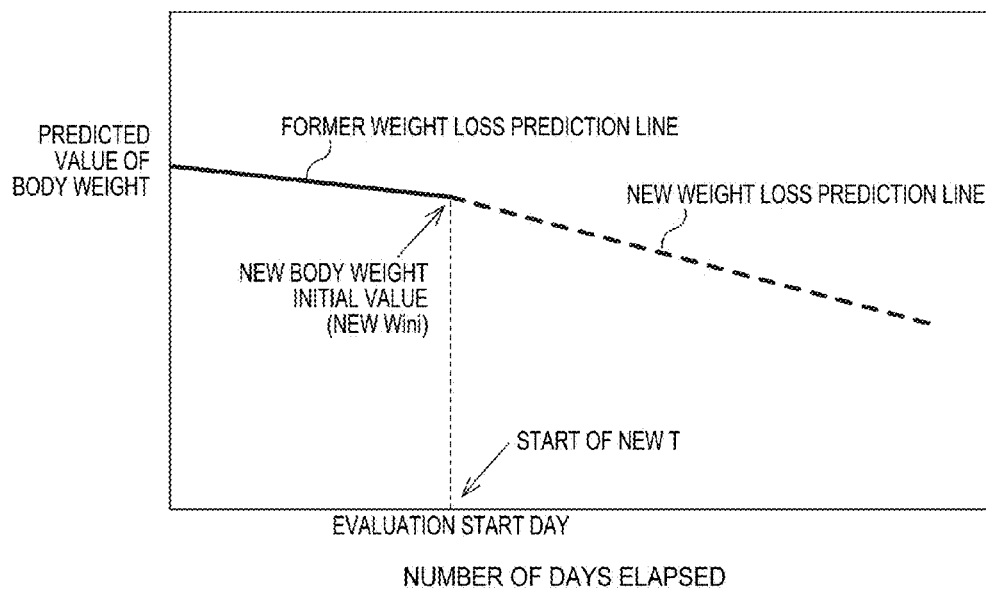
FIG. 13 illustrates target resetting processing.

That is, the target setting processing carried out at the start of the use of the service is not limited to this timing and may also be carried out at any timing intended by the user. The specific processing content is similar to the processing described above and therefore will not be described further in detail. However, in the equation (3), $W_{ini}$ is not the value at the start of the advice period, and the actually measured value at the time of checking the status of progress, or the latest measured value is used, as shown in FIG. 13. Also, the target period T needs to be changed to a period that starts at the point of checking the status of progress.

FIG. 13 illustrates the target resetting processing.

Figure 14:
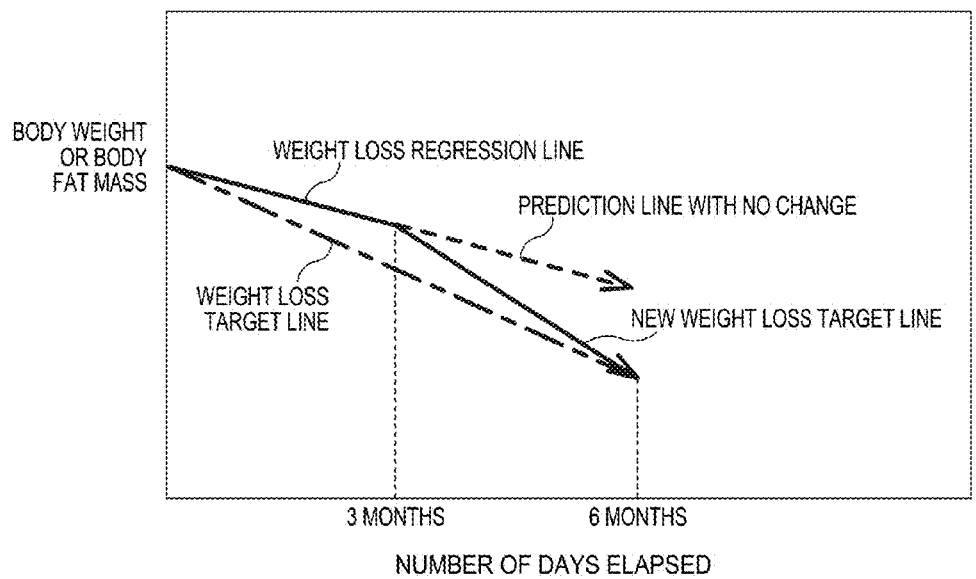
FIG. 14 is another chart illustrating target resetting processing.

The processing up to this point is illustrated in FIG. 14.

FIG. 14 is another view illustrating the target resetting processing. Specifically, FIG. 14 corresponds to an example in which, since the pace of weight loss is slow up to a halfway point, the zone staying time after the point of checking the status of progress has a greater value than the initial zone staying time, thus changing to a harder target.

Figure 15:
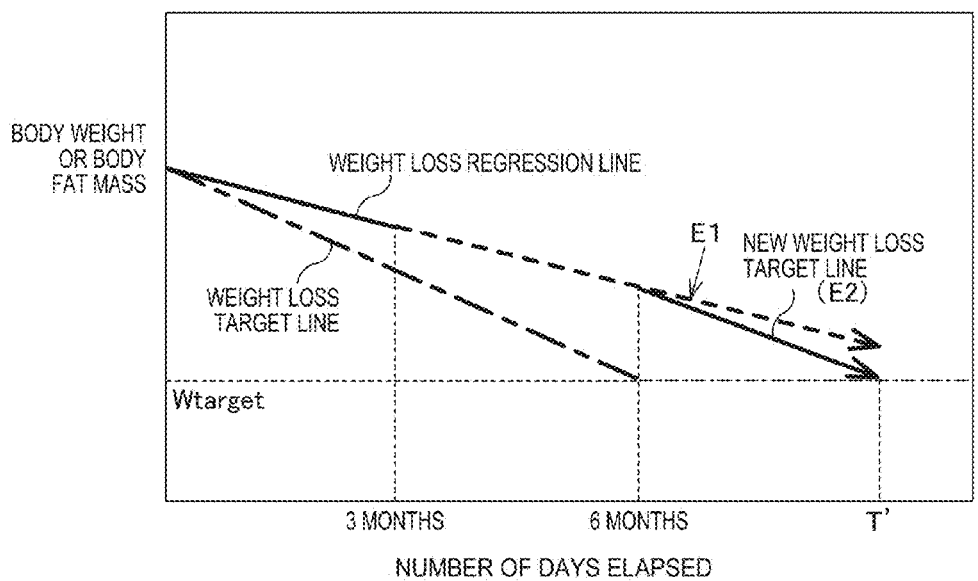
FIG. 15 illustrates processing when an advice period ends.

Also, the advice information generation processing and the target resetting processing using the equation (3) or the like may be carried out when the target period is reached, as shown in FIG. 15.

FIG. 15 illustrates the processing when the target period is reached. The example of FIG. 15 represents the case where the initial target cannot be achieved even after the target period of six months.

For example, in the example of FIG. 15, the regression line found from the actually measured value of weight loss during the target period is extended as indicated by E1. Thus, the period or the like required to achieve the original target body weight $W_{target}$ in the case where similar levels of exercise are continued, is generated and presented to the user. Alternatively, a proper target timing T' may be set and a new weight loss target line E2 to achieve the original target body weight $W_{target}$ by the target timing T' may be set. As described above using the equation (3) or the like, if a target line is set, the zone staying time T_zone required to achieve the target line can be found, and the resulting zone staying time T_zone can be presented as advice information.

Next, target resetting processing carried out by the user will be described.

Figure 16:
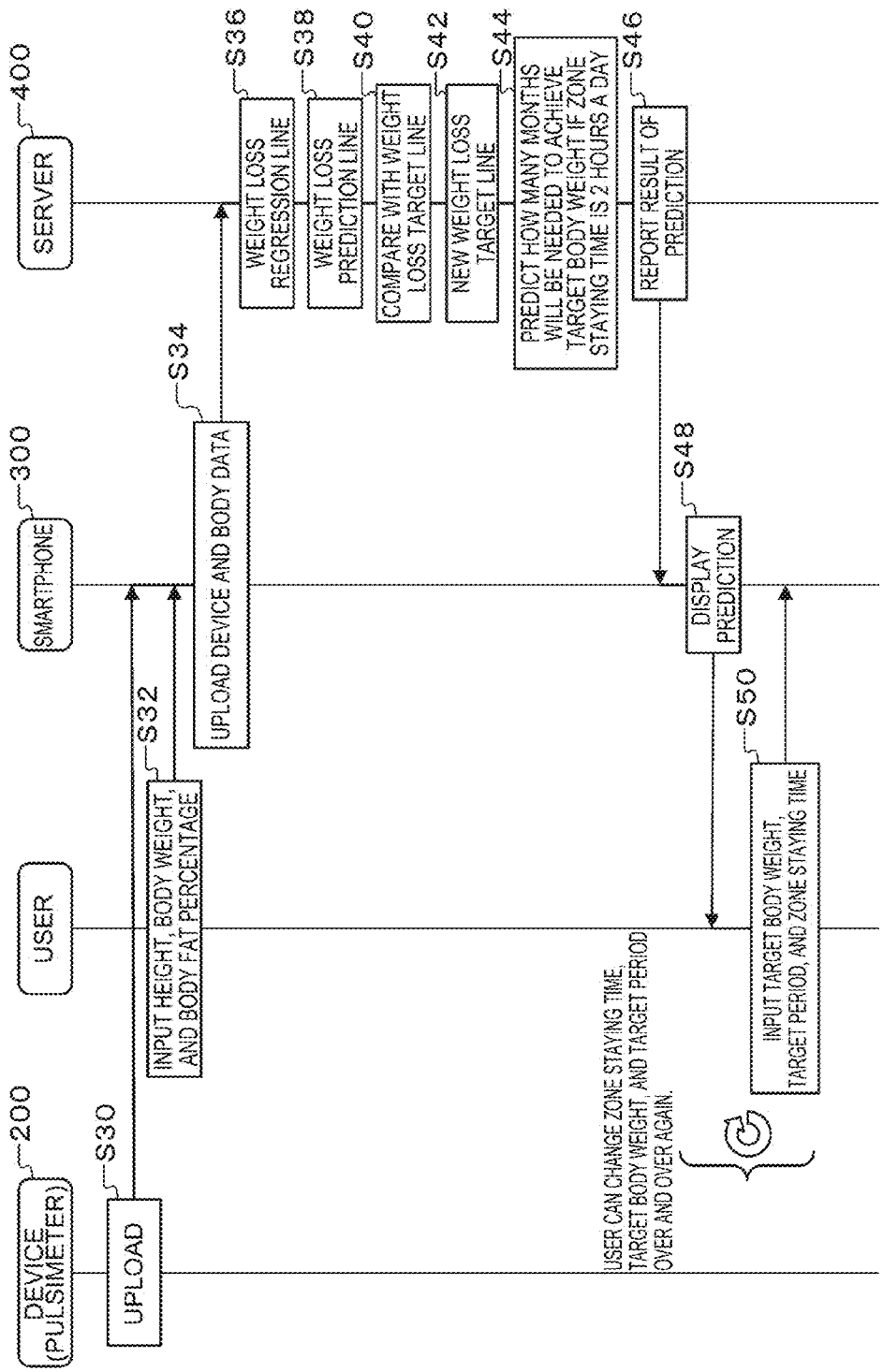
FIG. 16 is a flowchart illustrating target resetting processing.

FIG. 16 is a flowchart illustrating the target resetting processing. First, in Step S30, the device (pulsimeter) 200 uploads data of the device to the smartphone 300.

Next, in Step S32, the user inputs the height, body weight and body fat percentage to the smartphone 300.

Subsequently, in Step S34, the smartphone 300 uploads the device and body data to the server system 400.

Next, in Step S36, the server system 400 finds a regression line E1 for weight loss on the basis of the actually measured value of body weight (weight loss regression line).

Subsequently, in Step S38, the server system 400 finds a weight loss prediction line on the basis of the same zone staying time as before (prediction line with no change).

Next, in Step S40, the server system 400 compares the prediction line with a weight loss target line.

Then, in Step 42, the server system 400 calculates the zone staying time per day so that the weight loss target can be achieved in next three months (new weight loss target line E2).

Next, in Step S44, in the case where the zone staying time per day is two hours or longer (unrealistic value), the server system 400 predicts how many months will be needed to achieve the target body weight if the zone staying time is two hours a day.

Subsequently, in Step S46, the server system 400 reports the result of the prediction to the smartphone 300. For example, the result of the prediction is data of 15 rows by 15 columns, coordinates, and an equation or the like.

Next, in Step S48, the smartphone 300 displays the prediction on the display unit 340 on the basis of the result of the prediction reported from the server system 400.

Then, in Step S50, the user inputs a zone staying time, a target body weight and a target period to the smartphone 300 according to need. The processing then returns to Step S48. Steps S48 and S50 are repeated every time the user changes the zone staying time, the target body weight and the target period.

Figure 17:
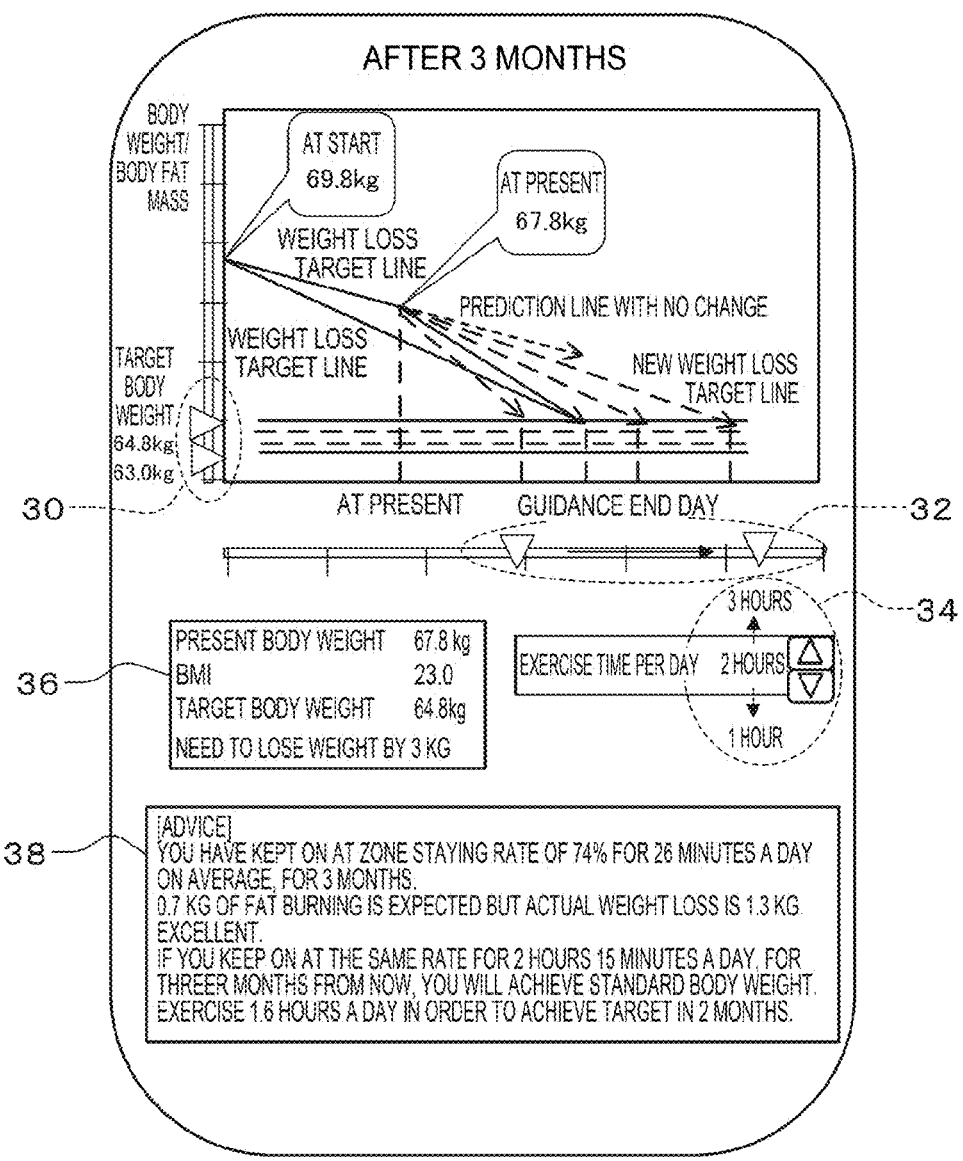
FIG. 17 is another chart illustrating target resetting processing.

FIG. 17 is another view illustrating the target resetting processing. A graph of a weight loss target line which predicts a weight loss during the period (for example, after three months) is displayed on the display unit 340 of the smartphone 300. The vertical axis represents the body weight/body fat mass and the target body weight. The horizontal axis represents the target period.

The weight loss regression line is found on the basis of the actually measured value of body weight. The prediction line with no change is a weight loss prediction line with the same zone staying time as before. The new weight loss target line is a new target line to achieve the weight loss target in the next three months.

For example, the graph of the weight loss target line shown in FIG. 17 shows that the target line starting at the present body weight of 67.8 kg changes in its gradient, depending on each target period. The target period shown in the area 32 may be changed by the user. Here, it is shown that the target period is changed in such a way as to have a zone staying time of two hours.

Figure 18:
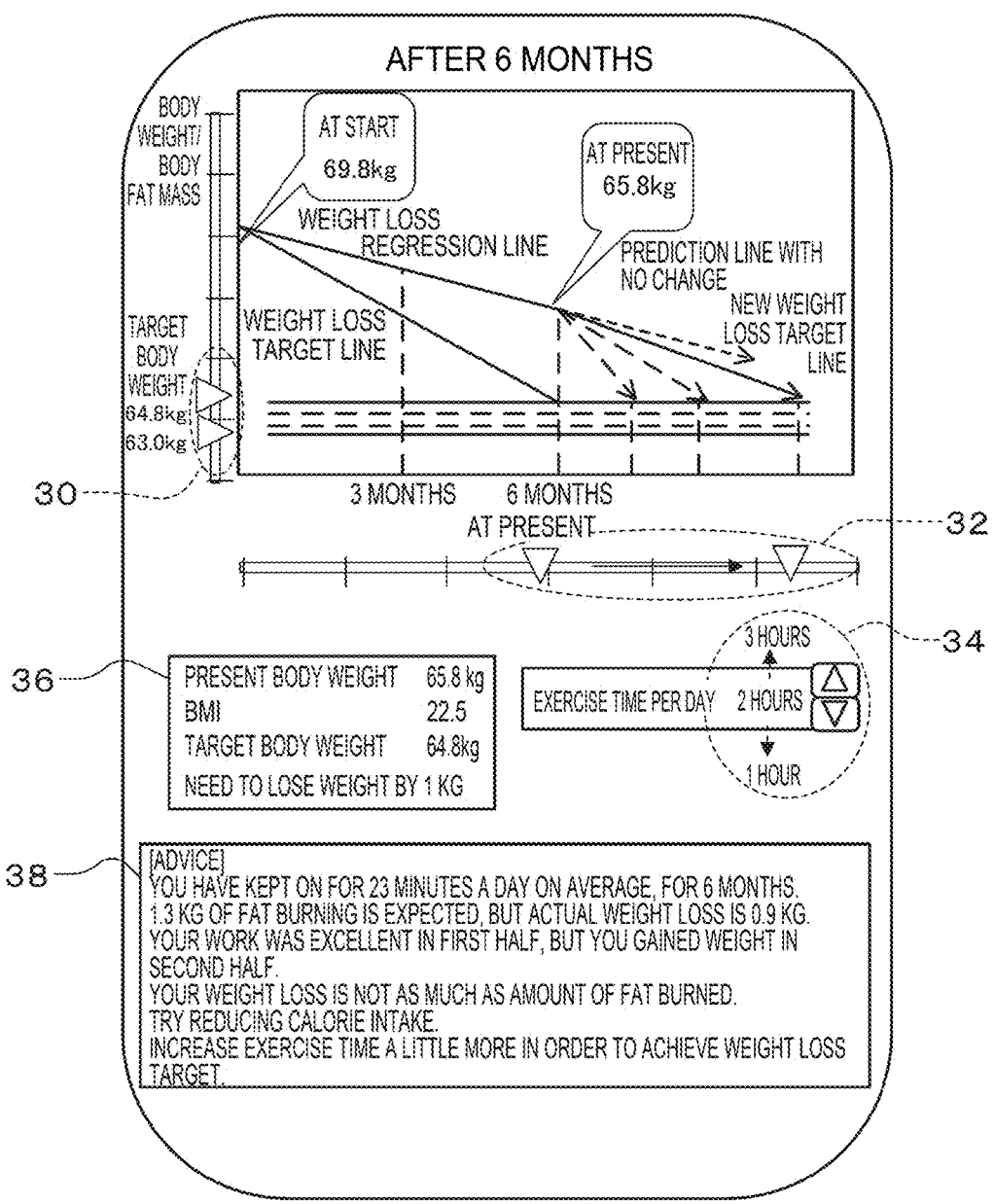
FIG. 18 illustrates processing when an advice period ends.

FIG. 18 illustrates processing at the end of the advice period. A graph of a weight loss target line which predicts a weight loss at the end of the period (for example, after six months) is displayed on the display unit 340 of the smartphone 300. The vertical axis represents the body weight/body fat mass and the target body weight. The horizontal axis represents the target period.

The new weight loss target line is a new target line to achieve the weight loss target with a zone staying time of two hours. For example, the graph of the weight loss target line shown in FIG. 18 shows that the target line starting at the present body weight of 65.8 kg changes in its gradient, depending on each target period.

According to this embodiment, the user can change the target value, the target period and the zone staying time by himself/herself, and therefore the target can be made visible. Since assistance can be provided in reasonable and effective target setting in which an achievable target for the user is set, the user will be motivated further. For example, since a target value of body weight or body fat mass and a target period are fixed and a zone staying time corresponding to each measured body information is calculated, target setting in which a value involved in target calculation such as a decision on a target value based on the target period and the zone staying time is changed flexibly, can be realized. Also, body weight and body fat mass can be predicted without re-measurement. Moreover, a predictive simulation can be conducted before an exercise is carried out.

4.3 Modifications

The value expressed by the pulse wave information according to the embodiment may be a pulse rate, in a narrow sense. However, this is not limiting. For example, the pulse wave information may be information of the frequency or the like of an AC component of a pulse wave signal. The fat burning zone is a range that is decided on the basis of a value expressed by a standard pulse wave signal and that is suitable for fat burning. For example, if the value expressed by the pulse wave signal is a pulse rate, the fat burning zone is a numerical range of pulse rate suitable for fat burning. Various techniques for finding a pulse rate (heart rate) suitable for fat burning are known, such as the Karvonen formula, and therefore will not be described in detail. Also, various arbitrary techniques can be applied as techniques for deciding the fat burning zone in the embodiment, and the decision is not limited to any particular technique. The staying time information may be any information that represents a time during which the value expressed by the pulse wave signal is within the fat burning zone. The staying time information may be the cumulative value of the zone staying time or may be the zone staying time during a unit period (for example, a day or a week). The staying time information may also be the zone staying rate, which is the rate of the zone staying time in a unit time (for example, an hour). The body information is information such as the body weight, body fat mass or the like of the user. In a broad sense, the body information may include information such as sex, height, and age. The target information is information representing a weight loss target, such as a target value of body weight, a target value of weight loss, or a target period to achieve a weight loss.

Thus, by acquiring at least two of the staying time information (exercise information), the body information and the target information, and then carrying out processing using a relational expression between the staying time information and body weight fluctuation (or fluctuation in body fat), it is possible to generate advice information. Therefore, the resulting information is generated in terms of the staying time information, and for example, a zone staying time or the like required to achieve a target body weight within a target period is presented. Therefore, when a weight loss is to be realized through exercise, excessive exercising in which the pulse rate exceeds the upper limit of the fat burning zone, and occurrence of injuries due to excessive exercising, or the like can be restrained. Also, by properly setting the fat burning zone, exercise with a load that enables efficient fat burning can be executed. Moreover, since loss of motivation due to setting of an excessive exercise target or the like can be restrained, continuous use of the service can be realized.

As a representative circumstance where the information processing system 100 of this embodiment is used, a training device in a fitness gym or the like may be considered.

Also, the graphs of the weight loss target line shown in FIGS. 10 and 17 show that the target line changes in its gradient, depending on each target period. However, a plurality of target lines with different gradients may be displayed simultaneously so that the user can select from these target lines.

In the information processing system 100 of the embodiment, a part or the majority of the processing may be realized by a program. In such a case, the information processing system 100 of the embodiment or the like is realized as a processor such as CPU executes the program. Specifically, an information processing method in which a program stored in a non-temporary information storage medium is read out and in which a processor such as CPU executes the program thus read out, is used. Here, the information storage medium (computer-readable medium) stores a program, data or the like, and the function thereof can be realized by an optical disk (DVD, CD or the like), HDD (hard disk drive), or memory (card memory, ROM, or the like) or the like. The processor such as CPU then carries out the various kinds of processing of the embodiment on the basis of the program (data) stored in the information storage medium. That is, a program for causing a computer (device having an operation unit, a processing unit, a storage unit and an output unit) to function as each unit of the embodiment (program for causing a computer to execute processing by each unit) is stored in the information storage medium.

The embodiment is described above in detail. However, a person skilled in the art will readily understand that a number of modifications can be made without substantially departing from the new matters and effects of the invention. Therefore, all such modifications are considered as included in the scope of the invention. For example, a term that is described along with a different term with a broader meaning or the same meaning at least once in the specification or drawings can be replaced with the different term at any part of the specification or drawings. Also, the configurations and operations of the information processing system and the like are not limited to those described in the embodiment and various modifications can be made thereto.

What is claimed is:

1. An information processing device for graphically updating progress and a prediction of weight loss or body fat loss of a user, comprising:
    a display unit; and
    a processor comprising:
        a user information acquisition unit which acquires:
            first information comprising a first target period,
            second information comprising a first current weight of the user or a first current body fat of the user, and
            third information comprising a heart rate zone staying time acquired from a pulse wave sensor;
        a correlation information acquisition unit which acquires correlation information representing a relation between heart rate zone staying time and amount of body fat lost per a unit of time;
        a prediction module which generates a prediction line of user body weight or user body fat over the first target period from the first current weight or the first current body fat to a target weight or a target body fat using the first information, the second information, the third information and the correlation information, and outputs the prediction line to be displayed as a first line on a graph on the display unit;
        a change designation unit which designates change of the second information from the first current weight or the first current body fat to a second current weight or a second current body fat;
        an update unit which updates the first information from the first target period to a second target period on the basis of the correlation information; and
        a progress module which generate a progress line of user body weight or user body fat from the first current weight or first current body fat to the second current weight or second current body fat, and outputs the progress line to be displayed as a second line on the graph on the display unit;
    wherein the prediction module generates a second prediction line of user body weight or user body fat over the second target period from the second current weight or second current body fat to a second target weight or a second target body fat using the first information, the second information, the third information and the correlation information, and outputs the second prediction line to be displayed as a third line on the graph on the display unit.

2. The information processing device according to claim 1, further comprising a communication unit,
    wherein the correlation information acquisition unit acquires the correlation information from the communication unit.

3. The information processing device according to claim 1, further comprising a fixing designation unit which designates fixing of the target weight or target body fat generated by the prediction module.

4. A method for graphically updating progress and a prediction of weight loss or body fat loss of a user, comprising:
    acquiring user information with a processor, the user information comprising:
        first information comprising a first target period, second information comprising a first current weight of the user or a first current body fat of the user, and third information comprising a heart rate zone staying time acquired from a pulse wave sensor;

acquiring correlation information, with a correlation information acquisition unit of the processor, wherein the correlation information represents a relation between heart rate zone staying time and amount of body fat lost per a unit of time;

generating, with a prediction module of the processor, a prediction line of user body weight or user body fat over the first target period from the first current weight or the first current body fat to a target weight or a target body fat using the first information, the second information, the third information and the correlation information, and outputting the prediction line to be displayed as a first line on a graph on the display unit;

designating, with a change designation unit of the processor, a change of the second information from the first current weight or the first current body fat to a second current weight or a second current body fat;

updating, with an update unit of the processor, the first information from the first target period to a second target period on the basis of the correlation information; and generating, with a progress module of the processor, a progress line of user body weight or user body fat from the first current weight or first current body fat to the second current weight or second current body fat, and outputting the progress line to be displayed as a second line on the graph on the display unit;

wherein the prediction module generates a second prediction line of user body weight or user body fat over the second target period from the second current weight or second current body fat to a second target weight or a second target body fat using the first information, the second information, the third information and the correlation information, and outputs the second prediction line to be displayed as a third line on the graph on the display unit.

5. The method according to claim 4, further comprising:
acquiring, with the information acquisition unit, the correlation information from a communication unit.

6. The method according to claim 4, further comprising:
designating fixing of the target weight or target body fat generated by the prediction module with a fixing designation unit of the processor.

7. A system for graphically updating progress and a prediction of weight loss or body fat loss of a user, comprising:

one or more processors configured for:

acquiring user information, the user information comprising:

first information comprising a first target period, second information comprising a first current weight of the user or a first current body fat of the user, and third information comprising a heart rate zone staying time acquired from a pulse wave sensor;

acquiring correlation information, wherein the correlation information represents a relation between heart rate zone staying time and amount of body fat lost per a unit of time; generating a prediction line of user body weight or user body fat over the first target period from the first current weight or the first current body fat to a target weight or a target body fat using the first information, the second information, the third information and the correlation information, and outputting the prediction line to be displayed as a first line on a graph on a display unit;

designating a change of the second information from the first current weight or the first current body fat to a second current weight or a second current body fat;

updating the first information from the first target period to a second target period on the basis of the correlation information;

generating a progress line of user body weight or user body fat from the first current weight or first current body fat to the second current weight or second current body fat, and outputting the progress line to be displayed as a second line on the graph on the display unit; and generating a second prediction line of user body weight or user body fat over the second target period from the second current weight or second current body fat to a second target weight or a second target body fat using the first information, the second information, the third information and the correlation information, and outputs the second prediction line to be displayed as a third line on the graph on the display unit.

8. The system according to claim 7, wherein the one or more processors are further configured for acquiring the correlation information from a communication unit.

9. The system according to claim 7, wherein the one or more processors are further configured for designating fixing of the target weight or target body fat.

* * * * *